United States Patent
Park et al.

(10) Patent No.: US 11,833,346 B2
(45) Date of Patent: Dec. 5, 2023

(54) INTEGRATED CIRCUITS FOR NEUROTECHNOLOGY AND OTHER APPLICATIONS

(71) Applicant: President and Fellows of Harvard College, Cambridge, MA (US)

(72) Inventors: Hongkun Park, Cambridge, MA (US); Donhee Ham, Cambridge, MA (US); Jeffrey T. Abbott, Cambridge, MA (US); Ling Qin, Cambridge, MA (US); Marsela Jorgolli, Cambridge, MA (US); Tianyang Ye, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 182 days.

(21) Appl. No.: 17/144,387

(22) Filed: Jan. 8, 2021

(65) Prior Publication Data
US 2021/0187280 A1    Jun. 24, 2021

Related U.S. Application Data

(63) Continuation of application No. 15/542,197, filed as application No. PCT/US2016/012685 on Jan. 8, 2016, now abandoned.
(Continued)

(51) Int. Cl.
*A61N 1/05* (2006.01)
*H01L 23/48* (2006.01)
(Continued)

(52) U.S. Cl.
CPC ............. *A61N 1/0531* (2013.01); *A61N 1/05* (2013.01); *A61N 1/0536* (2013.01); *A61N 1/06* (2013.01);
(Continued)

(58) Field of Classification Search
CPC ...... A61N 1/0531; A61N 1/05; A61N 1/0536; A61N 1/06; B82Y 5/00; H01L 23/48;
(Continued)

(56) References Cited

U.S. PATENT DOCUMENTS

| | | |
|---|---|---|
| 5,072,194 A | 12/1991 | Chevallier |
| 5,233,985 A | 8/1993 | Hudrlik |

(Continued)

FOREIGN PATENT DOCUMENTS

| | | |
|---|---|---|
| DE | 19529371 C2 | 1/1998 |
| EP | 1 271 144 A1 | 1/2003 |

(Continued)

OTHER PUBLICATIONS

U.S. Appl. No. 15/542,197, filed Jul. 7, 2017, Park et al.
(Continued)

*Primary Examiner* — Matthew D Krcha
*Assistant Examiner* — Jacqueline Brazin
(74) *Attorney, Agent, or Firm* — Wolf, Greenfield & Sacks, P.C.

(57) ABSTRACT

The present invention generally relates to nanowires. In one aspect, the present invention is generally directed to systems and methods of individually addressing nanowires on a surface, e.g., that are substantially upstanding or vertically-oriented with respect to the surface. In some cases, one or more nanowires may be individually addressed using various integrated circuit ("IC") technologies, such as CMOS. For example, the nanowires may form an array on top of an active CMOs integrated circuit.

19 Claims, 28 Drawing Sheets

Related U.S. Application Data

(60) Provisional application No. 62/126,402, filed on Feb. 27, 2015, provisional application No. 62/101,931, filed on Jan. 9, 2015.

(51) Int. Cl.
| | |
|---|---|
| *H01L 29/06* | (2006.01) |
| *A61N 1/06* | (2006.01) |
| *B82Y 5/00* | (2011.01) |
| *H01L 23/49* | (2006.01) |

(52) U.S. Cl.
CPC ............. *B82Y 5/00* (2013.01); *H01L 23/48* (2013.01); *H01L 23/49* (2013.01); *H01L 29/0676* (2013.01); *H01L 2924/0002* (2013.01); *H01L 2924/10253* (2013.01); *H01L 2924/14* (2013.01)

(58) Field of Classification Search
CPC ............. H01L 23/49; H01L 29/0676; H01L 2924/0002; H01L 2924/10253; H01L 2924/14; G01N 33/48728
USPC ...................................................... 422/82.01
See application file for complete search history.

(56) References Cited

U.S. PATENT DOCUMENTS

| | | | |
|---|---|---|---|
| 5,381,753 A | 1/1995 | Okajima et al. | |
| 5,605,612 A | 2/1997 | Park et al. | |
| 5,688,642 A | 11/1997 | Chrisey et al. | |
| 5,858,862 A | 1/1999 | Westwater et al. | |
| 6,123,819 A | 9/2000 | Peeters | |
| 6,286,226 B1 | 9/2001 | Jin | |
| 7,163,659 B2 | 1/2007 | Stasiak et al. | |
| 7,332,313 B2 | 2/2008 | Giaever et al. | |
| 7,795,039 B2 | 9/2010 | Spira et al. | |
| 8,159,300 B2 | 4/2012 | Masuda et al. | |
| 8,227,223 B2 | 7/2012 | Giaever et al. | |
| 8,993,327 B2 | 3/2015 | McKnight et al. | |
| 9,304,132 B2 | 4/2016 | Park et al. | |
| 9,360,469 B1 | 6/2016 | Clements et al. | |
| 9,700,221 B2 | 7/2017 | Rajaraman et al. | |
| 9,983,198 B2 | 5/2018 | Chvatal et al. | |
| 11,167,131 B2 | 11/2021 | Isaacs et al. | |
| 2002/0010415 A1 | 1/2002 | Simon et al. | |
| 2002/0045318 A1 | 4/2002 | Chen et al. | |
| 2002/0190732 A1 | 12/2002 | Cheng et al. | |
| 2003/0027327 A1 | 2/2003 | Cunningham et al. | |
| 2003/0100189 A1 | 5/2003 | Lee et al. | |
| 2003/0189202 A1 | 10/2003 | Li et al. | |
| 2004/0100290 A1 | 5/2004 | Pope et al. | |
| 2004/0106203 A1 | 6/2004 | Stasiak et al. | |
| 2004/0182707 A1 | 9/2004 | Jardemark et al. | |
| 2004/0197909 A1 | 10/2004 | McKnight et al. | |
| 2005/0170510 A1 | 8/2005 | Huang et al. | |
| 2005/0221072 A1 | 10/2005 | Dubrow et al. | |
| 2005/0253137 A1 | 11/2005 | Whang et al. | |
| 2005/0282284 A1 | 12/2005 | Rubinsky et al. | |
| 2006/0121446 A1 | 6/2006 | Abassi et al. | |
| 2006/0177464 A1 | 8/2006 | Schneewind et al. | |
| 2006/0214156 A1 | 9/2006 | Pan et al. | |
| 2006/0275800 A1 | 12/2006 | Doecke et al. | |
| 2007/0072257 A1 | 3/2007 | Negulescu et al. | |
| 2007/0087401 A1 | 4/2007 | Neilson et al. | |
| 2007/0187840 A1 | 8/2007 | Dell'Acqua-Bellavitis et al. | |
| 2007/0264634 A1 | 11/2007 | Bock et al. | |
| 2008/0009434 A1* | 1/2008 | Reches ............... C12Q 1/6869 | |
| | | | 623/23.72 |
| 2008/0218939 A1 | 9/2008 | Marcus et al. | |
| 2008/0248575 A1 | 10/2008 | Lee et al. | |
| 2009/0227066 A1 | 9/2009 | Joseph et al. | |
| 2009/0242405 A1 | 10/2009 | Mayer et al. | |
| 2009/0255801 A1 | 10/2009 | Hass | |
| 2009/0312194 A1 | 12/2009 | Tyner et al. | |
| 2010/0038247 A1 | 2/2010 | Zimmermann et al. | |
| 2010/0140111 A1 | 6/2010 | Gimsa et al. | |
| 2010/0164110 A1* | 7/2010 | Jin ................ H01L 29/0657 | |
| | | | 257/757 |
| 2010/0213579 A1 | 8/2010 | Henry et al. | |
| 2010/0233226 A1 | 9/2010 | Ferain et al. | |
| 2010/0279513 A1 | 11/2010 | Niu et al. | |
| 2011/0006674 A1 | 1/2011 | Naaman et al. | |
| 2011/0064785 A1 | 3/2011 | Daniels et al. | |
| 2011/0104732 A1 | 5/2011 | Lucic et al. | |
| 2011/0210718 A1 | 9/2011 | Vana et al. | |
| 2011/0233512 A1 | 9/2011 | Yang et al. | |
| 2011/0253982 A1 | 10/2011 | Wang et al. | |
| 2011/0291643 A1 | 12/2011 | Ravindran et al. | |
| 2011/0309237 A1 | 12/2011 | Seo et al. | |
| 2012/0094328 A1 | 4/2012 | Park et al. | |
| 2012/0094382 A1 | 4/2012 | Park et al. | |
| 2012/0157804 A1* | 6/2012 | Rogers ............... H01L 24/50 | |
| | | | 604/20 |
| 2012/0182168 A1 | 7/2012 | Shibata et al. | |
| 2013/0041235 A1 | 2/2013 | Rogers et al. | |
| 2013/0072775 A1 | 3/2013 | Rogers et al. | |
| 2013/0115705 A1* | 5/2013 | Patolsky ............... G01N 27/00 | |
| | | | 422/82.01 |
| 2013/0123136 A1 | 5/2013 | Abassi et al. | |
| 2013/0260467 A1 | 10/2013 | Park et al. | |
| 2013/0266599 A1 | 10/2013 | Zimmerman | |
| 2013/0284612 A1 | 10/2013 | Park et al. | |
| 2013/0338746 A1 | 12/2013 | Guvanasen et al. | |
| 2013/0341734 A1 | 12/2013 | Merz | |
| 2014/0001041 A1 | 1/2014 | Rahman et al. | |
| 2014/0057283 A1 | 2/2014 | Wang et al. | |
| 2015/0005680 A1 | 1/2015 | Lipani | |
| 2015/0027885 A1 | 1/2015 | Rajaraman et al. | |
| 2015/0148863 A1 | 5/2015 | Yun et al. | |
| 2015/0191688 A1 | 7/2015 | Park et al. | |
| 2015/0197807 A1 | 7/2015 | Park et al. | |
| 2015/0203348 A1 | 7/2015 | Park et al. | |
| 2015/0376811 A1 | 12/2015 | Joung et al. | |
| 2015/0377856 A1 | 12/2015 | Dunbar et al. | |
| 2016/0047770 A1 | 2/2016 | Tyler et al. | |
| 2016/0096173 A1 | 4/2016 | Teich et al. | |
| 2016/0245790 A1 | 8/2016 | Kawai et al. | |
| 2016/0278713 A1 | 9/2016 | Shoaran et al. | |
| 2016/0281110 A1 | 9/2016 | Park et al. | |
| 2017/0058246 A1 | 3/2017 | Grier, Jr. et al. | |
| 2017/0176414 A1 | 6/2017 | Abdolahad et al. | |
| 2017/0336384 A1 | 11/2017 | Ino et al. | |
| 2018/0119172 A1 | 5/2018 | Park et al. | |
| 2018/0163165 A1 | 6/2018 | Grier, Jr. et al. | |
| 2018/0169403 A1 | 6/2018 | Park et al. | |
| 2020/0064336 A1 | 2/2020 | Zafar et al. | |
| 2020/0292482 A1 | 9/2020 | Ham et al. | |
| 2021/0236033 A1 | 8/2021 | Butera et al. | |
| 2021/0371846 A1 | 12/2021 | Ham et al. | |
| 2022/0397512 A1 | 12/2022 | Ham et al. | |
| 2023/0014082 A1 | 1/2023 | Ham et al. | |

FOREIGN PATENT DOCUMENTS

| | | |
|---|---|---|
| EP | 2 447 354 A1 | 5/2012 |
| JP | H10-234366 A | 9/1998 |
| JP | 2001-153738 A | 6/2001 |
| JP | 2004-184414 A | 7/2004 |
| JP | 2007-519405 A | 7/2007 |
| JP | 2008-269725 A | 11/2008 |
| JP | 2011-500184 A | 1/2011 |
| JP | 2012-501642 A | 1/2012 |
| WO | WO 2003/013647 A1 | 2/2003 |
| WO | WO 2004/036202 A1 | 4/2004 |
| WO | WO 2005/066342 A1 | 7/2005 |
| WO | WO 2005/075656 A1 | 8/2005 |
| WO | WO 2005/093831 A1 | 10/2005 |
| WO | WO 2006/001614 A1 | 1/2006 |
| WO | WO 2008/018834 A1 | 2/2008 |
| WO | WO 2009/050168 A1 | 4/2009 |
| WO | WO 2009/104056 A1 | 8/2009 |
| WO | WO 2009/137440 A1 | 11/2009 |

(56) References Cited

FOREIGN PATENT DOCUMENTS

| WO | WO 2010/003062 A2 | 1/2010 |
|---|---|---|
| WO | WO 2010/026450 A1 | 3/2010 |
| WO | WO 2010/121130 A2 | 10/2010 |
| WO | WO 2012/050876 | 4/2012 |
| WO | WO 2012/050881 | 4/2012 |
| WO | WO 2014/031171 A1 | 2/2014 |
| WO | WO 2014/031172 A1 | 2/2014 |
| WO | WO 2016/112315 | 7/2016 |
| WO | WO 2019/010343 A1 | 1/2019 |
| WO | WO 2019/089495 A1 | 5/2019 |
| WO | WO 2021/257686 A1 | 12/2021 |
| WO | WO 2021/257701 A1 | 12/2021 |
| WO | WO 2021/257705 A1 | 12/2021 |

OTHER PUBLICATIONS

U.S. Appl. No. 16/760,723, filed Apr. 30, 2020, Ham et al.
U.S. Appl. No. 16/625,603, filed Dec. 20, 2019, Abbott et al.
PCT/US2010/031392, Aug. 16, 2011, International Search Report and Written Opinion.
PCT/US2010/031392, Oct. 27, 2011, International Preliminary Report on Patentability.
PCT/US2011/053640, Sep. 25, 2012, International Search Report and Written Opinion.
PCT/US2011/053640, Apr. 11, 2013, International Preliminary Report on Patentability.
CN 201180051218.4, May 23, 2014, Office Action.
CN 201180051218.4, Oct. 30, 2014, Office Action.
CN 201180051218.4, Feb. 9, 2015, Office Action.
EP 11770260.5, Jul. 3, 2015, Office Action.
EP 16179425.0, Oct. 11, 2016, Extended European Search Report.
JP 2013-531762, Jun. 23, 2015, Office Action.
JP 2013-531762, Mar. 8, 2016, Office Action.
SG 201302254-6, Jun. 30, 2014, Search Report and Written Opinion.
SG 201302254-6, Jan. 30, 2015, Examination Report.
PCT/US2011/053646, Jul. 11, 2012, International Search Report.
PCT/US2011/053646, Apr. 11, 2013, International Preliminary Report on Patentability.
PCT/US2013/032457, Jun. 10, 2013, International Search Report and Written Opinion.
PCT/US2013/032457, Mar. 5, 2015, International Preliminary Report on Patentability.
PCT/US2013/032486, Sep. 17, 2013, International Search Report and Written Opinion.
PCT/US2013/032486, Mar. 5, 2015, International Preliminary Report on Patentability.
PCT/US2013/032512, Aug. 1, 2013, International Search Report and Written Opinion.
PCT/US2013/032512, Mar. 5, 2015, International Preliminary Report on Patentability.
PCT/US2016/012685, Feb. 24, 2016, Invitation to Pay Additional Fees.
PCT/US2016/012685, May 3, 2016, International Search Report and Written Opinion.
PCT/US2016/012685, Jul. 20, 2017, International Preliminary Report on Patentability.
PCT/US18/58081, Jan. 15, 2019, Invitation to Pay Additional Fees.
PCT/US18/58081, Mar. 22, 2019, International Search Report and Written Opinion.
PCT/US18/58081, May 14, 2020, International Preliminary Report on Patentability.
PCT/US18/40969, Aug. 31, 2018, Invitation to Pay Additional Fees.
PCT/US18/40969, Nov. 2, 2018, International Search Report and Written Opinion.
PCT/US18/40969, Jan. 16, 2020, International Preliminary Report on Patentability.
International Search Report and Written Opinion for Application No. PCT/US2010/031392 dated Aug. 16, 2011.
International Preliminary Report on Patentability for Application No. PCT/US2010/031392 dated Oct. 27, 2011.
International Search Report and Written Opinion for Application No. PCT/US2011/053640 dated Sep. 25, 2012.
International Preliminary Report on Patentability for Application No. PCT/US2011/053640 dated Apr. 11, 2013.
Chinese Office Action dated May 23, 2014 for Application No. 201180051218.4.
Chinese Office Action dated Oct. 30, 2014 for Application No. 201180051218.4.
Chinese Office Action dated Feb. 9, 2015 for Application No. 201180051218.4.
European Office Action dated Jul. 3, 2015 for Application No. 11770260.5.
Extended European Search Report for Application No. EP 16179425.0 dated Oct. 11, 2016.
Japanese Office Action dated Jun. 23, 2015 for Application No. 2013-531762.
Japanese Office Action dated Mar. 8, 2016 for Application No. 2013-531762.
Singapore Search Report and Written Opinion dated Jun. 30, 2014 for Application No. SG 201302254-6.
Singapore Examination Report dated Jan. 30, 2015 for Application No. 201302254-6.
International Search Report and Written Opinion for Application No. PCT/US2011/053646 dated Jul. 11, 2012.
International Preliminary Report on Patentability for Application No. PCT/US2011/053646 dated Apr. 11, 2013.
International Search Report and Written Opinion for Application No. PCT/US2013/032457 dated Jun. 10, 2013.
International Preliminary Report on Patentability for Application No. PCT/US2013/032457 dated Mar. 5, 2015.
International Search Report and Written Opinion for Application No. PCT/US2013/032486 dated Sep. 17, 2013.
International Preliminary Report on Patentability for Application No. PCT/US2013/032486 dated Mar. 5, 2015.
International Search Report and Written Opinion for Application No. PCT/US2013/032512 dated Aug. 1, 2013.
International Preliminary Report on Patentability for Application No. PCT/US2013/032512 dated Mar. 5, 2015.
Invitation to Pay Additional Fees for Application No. PCT/US2016/012685 dated Feb. 24, 2016.
International Search Report and Written Opinion for Application No. PCT/US2016/012685 dated May 3, 2016.
International Preliminary Report on Patentability for PCT/US2016/012685 dated Jul. 20, 2017.
Invitation to Pay Additional Fees for Application No. PCT/US18/58081 dated Jan. 1, 2019.
International Search Report and Written Opinion for Application No. PCT/US18/58081 dated Mar. 22, 2019.
International Preliminary Report on Patentability for Application No. PCT/US18/58081 dated May 14, 2020.
Invitation to Pay Additional Fees for Application No. PCT/US18/40969 dated Aug. 31, 2018.
International Search Report and Written Opinion for Application No. PCT/US18/40969 dated Nov. 2, 2018.
International Preliminary Report on Patentability for Application No. PCT/US18/40969 dated Jan. 16, 2020.
[No Author Listed] NeonTM Transfection System Product Information at <http://www.lifetechnologies.com/us/en/home/life-science/cell-culture/transfection/transfection---selection-misc/neon-transfection-system/neon-transfection-system-information.html> Last accessed Sep. 27, 2013. Life Technologies Corporation. 2013.
[No Author Listed] Nuclearfector™ Kits for Rat Neurons at <http://www.lonza.com/products-services/bio-research/transfection/nucleofector-kits-for-primary-cells/nucleofector-kits-for-primary-neural-cells/nucleofector-kits-for-rat-neurons.aspx> Last accessed Sep. 30, 2013. Lonza Group Ltd. 2013.
Agarwal et al., Effect of cell size and shape on single-cell electroporation. Anal Chem. May 15, 2007;79(10):3589-96. Epub Apr. 20, 2007.
Berthing et al., Applications of nanowire arrays in nanomedicine. J Nanoneuroscience. May 2009;1(1):3-9.

(56) References Cited

OTHER PUBLICATIONS

Chang et al., Changes in membrane structure induced by electroporation as revealed by rapid-freezing electron microscopy. Biophysical Journal. Jul. 1990;58(1):1-12.
Chuang et al., Inhibition of CD36-dependent phagocytosis by prostaglandin E2 contributes to the development of endometriosis. Am J Pathol. Feb. 2010;176(2):850-60. Epub Dec. 24, 2009.
Crescentini et al., Noise limits of CMOS current interfaces for biosensors: a review. IEEE Trans Biomed Circuits Syst. 2014;8(2):278-292.
Gersten et al., Electromagnetic theory of enhanced Raman scattering by molecules adsorbed on rough surfaces. J Chem Phys. Oct. 1, 1980;73(7):3023. 15 pages.
Held et al. Microneedle arrays for intracellular recording applications. Micro Electro Mechanical Systems. MEMS 2008. IEEE 21s International Conference; Jan. 17, 2008; 13-17:268-271.
Hochbaum et al., Controlled growth of Si nanowire arrays for device integration. Nano Lett. Mar. 2005;5(3):457-60.
Hughes, Nanostructure-mediated drug delivery. Nanomedicine. Mar. 2005;1(1):22-30.
Hwang et al., High density n-Si/n-TiO2 core/shell nanowire arrays with enhanced photoactivity. Nano Lett. Jan. 2009;9(1):410-5. doi: 10.1021/n18032763.
Kim et al., An area-efficient low-noise CMOS DNA detection sensor for multichannel nanopore applications. Sensors and Actuators B: Chemical. Jan. 2013;176:1051-1055.
Kim et al., Interfacing silicon nanowires with mammalian cells. J Am Chem Soc. Jun. 13, 2007;129(23):7228-9. Epub May 22, 2007.
Lee et al., Layer-by-layer assembly of zeolite crystals on glass with polyelectrolytes as ionic linkers. J Am Chem Soc. Oct. 10, 2001;123(40):9769-79.
Lee et al., Vapor-liquid-solid and vapor-solid growth of phase-change Sb2Te3 nanowires and Sb2Te3/GeTe nanowire heterostructures. J Am Chem Soc. May 14, 2008;130(19):6252-8. Epub Apr. 11, 2008.
Martensson et al., Epitaxial III-V Nanowires on Silicon. Nano Letters. Sep. 2004;4(10):1987-90.
Meister et al., Mechanisms of gene silencing by double-stranded RNA. Nature. Sep. 16, 2004;431(7006):343-9. Review.
Okita et al., Generation of mouse induced pluripotent stem cells without viral vectors. Science. Nov. 7, 2008;322(5903):949-53. Epub Oct. 9, 2008.
Olofsson et al., Single-cell electroporation. Curr Opin Biotechnol. Feb. 2003;14(1):29-34.
Park et al., Selective surface functionalization of silicon nanowires via nanoscale joule heating. Nano Lett. Oct. 2007;7(10):3106-11. With supporting information.
Park, Vertical Nanowire Platform: Leveraging Semiconductor Technology to Develop Biological Tools. Seminar at Stanford. May 2012. Abstract.
Peng et al., Dendrite-assisted growth of silicon nanowires in electroless metal deposition. Adv Funct Mater. 2003; 13:127-132.
Peng et al., Fabrication of large-area silicon nanowire p-n junction diode arrays. Adv Mater. 2004; 16:73-76.
Raffa et al., Carbon nanotube-enhanced cell electropermeabilisation. Bioelectrochemistry. Aug. 2010;79(1):136-41. Epub Nov. 2, 2009.
Shalek et al., Chemical and electrical interrogation of biological networks using vertical nanowires. Pioneer Awards, NIH. Sep. 2011. Poster.
Shalek et al., Nanowire-mediated delivery enables functional interrogation of primary immune cells: application to the analysis of chronic lymphocytic leukemia. Nano Lett. Dec. 12, 2012;12(12):6498-504. Epub Dec. 3, 2012. With supporting information.
Shalek et al., Vertical silicon nanowires as a universal platform for delivering biomolecules into living cells. Proc Natl Acad Sci U S A. Feb. 2, 2010;107(5):1870-5. Epub Jan. 11, 2010.
Tsakalakos et al., Strong broadband optical absorption in silicon nanowire films. Journal of Nanophotonics. Jul. 17, 2007; 1:013552.
Van Tendeloo et al., Highly efficient gene delivery by mRNA electroporation in human hematopoietic cells: superiority to lipofection and passive pulsing of mRNA and to electroporation of plasmid cDNA for tumor antigen loading of dendritic cells. Blood. Jul. 1, 2001;98(1):49-56.
Vierbuchen et al., Direct conversion of fibroblasts to functional neurons by defined factors. Nature. Feb. 25, 2010;463(7284):1035-41. doi: 10.1038/nature08797. Epub Jan. 27, 2010.
Wang et al., Sensitivity to Wnt pathway inhibition in CLL is associated with specific gene expression signatures. Blood (ASH Annual Meeting Abstracts) Nov. 2011;118(21):364. Abstract 801.
Wokaun et al., Radiation damping in surface-enhanced Raman scattering. Phys Rev Lett. Apr. 5, 1982;48:957-60.
Xia et al., siRNA-mediated gene silencing in vitro and in vivo. Nat Biotechnol. Oct. 2002;20(10):1006-10. Epub Sep. 16, 2002.
Xu et al., Dependence of axon initial segment formation on Na+ channel expression. J Neurosci Res. Feb. 15, 2005;79(4):428-41.
Zhang et al., Large-area Silver-Coated Silicon Nanowire Arrays for Molecular Sensing Using Surgace-Enhanced Raman Spectroscopy. Adv Funct. Mater. 2008. 18: 2348-55.
Zhao et al., High-efficiency transfection of primary human and mouse T lymphocytes using RNA electroporation. Mol Ther. Jan. 2006; 13(1):151-9. Epub Sep. 2, 2005.
International Search Report and Written Opinion for Application No. PCT/US2021/037604 dated Sep. 29, 2021.
International Preliminary Report on Patentability for Application No. PCT/US2021/037604 dated Dec. 29, 2022.
International Search Report and Written Opinion for Application No. PCT/US2021/37626 dated Sep. 22, 2021.
International Preliminary Report on Patentability for Application No. PCT/US2021/37626 dated Dec. 29, 2022.
International Search Report and Written Opinion for Application No. PCT/US2021/037630 dated Sep. 28, 2021.
International Preliminary Report on Patentability No. PCT/US2021/037630 dated Dec. 29, 2022.
Abbott et al., CMOS nanoelectrode array for all-electrical intracellular electrophysiological imaging. Nat Nanotechnol. May 2017;12(5):460-466 and supplemental information. doi: 10.1038/nnano.2017.3. Epub Feb. 13, 2017. 37 pages.
Abbott et al., Multi-parametric functional imaging of cell cultures and tissues with a CMOS microelectrode array. Lab Chip. Mar. 29, 2022;22(7):1286-1296. doi: 10.1039/d11c00878a.
Giovangrandi et al., Low-cost microelectrode array with integrated heater for extracellular recording of cardiomyocyte cultures using commercial flexible printed circuit technology. Sensors and Actuators B 113. Apr. 22, 2015;113:545-554.
Jorgolli, Integrated Nanoscale Tools for Interrogating Living Cells. May 2015. Doctoral dissertation, Harvard University, Graduate School of Arts & Sciences.
Laborde et al., Real-time imaging of microparticles and living cells with CMOS nanocapacitor arrays. Nat Nanotechnol. Sep. 2015;10(9):791-5. doi: 10.1038/nnano.2015.163. Epub Aug. 3, 2015.
Park et al., 1024-Pixel CMOS Multimodality Joint Cellular Sensor/Stimulator Array for Real-Time Holistic Cellular Characterization and Cell-Based Drug Screening. IEEE Trans Biomed Circuits Syst. Feb. 2018; 12(1): 80-94. Author manuscript provided. 45 pages.

* cited by examiner

Deposit PECVD oxide directly on CMOS chips

Generate etch mask via stepper lithography

Dry SiOx etch (3um)
Thin down the SiOx tips via wet etch
Conformally coat the SiOx electrodes with metal $I_{mw}$ (A)

INTEGRATED CIRCUITS FOR NEUROTECHNOLOGY AND OTHER APPLICATIONS

RELATED APPLICATIONS

This application is a continuation of U.S. patent application Ser. No. 15/542,197, filed Jul. 7, 2017, entitled "Nanowire Arrays for Neurotechnology and Other Applications," which is a national phase entry of International Patent Application Serial No. PCT/US2016/012685, filed Jan. 8, 2016, entitled "Nanowire Arrays for Neurotechnology and Other Applications," by Park, et al., which claims the benefit of U.S. Provisional Patent Application Ser. No. 62/101,931, filed Jan. 9, 2015, entitled "Nanowire Arrays for Neurotechnology and Other Applications," by Park, et al.; and U.S. Provisional Patent Application Ser. No. 62/126,402, filed Feb. 27, 2015, entitled "Nanowire Arrays for Neurotechnology and Other Applications," by Park, et al., each of which is incorporated herein by reference in its entirety.

GOVERNMENT FUNDING

This invention was made with government support under Grant No. 8DP1DA035083-05 awarded by the National Institutes of Health and under Grant No. W911NF-15-1-0565 awarded by the U.S. Army Research Office. The government has certain rights in the invention.

FIELD

The present invention generally relates to nanowires.

BACKGROUND

To date, many neurological disorders remain poorly understood and lack therapeutic treatments despite research programs focusing on elucidating the cellular basis of the disorders and screening for potential new drugs. In part, this has been attributed to a shortage of drug screening assays that facilitate large-scale experiments with primary mammalian neurons.

Over the course of the last two decades, drugs targeting both voltage- and ligand-gated ion channels have been successfully developed to treat a broad range of neurological diseases. Despite their validated potential as druggable targets, ion-channel-targeted drug discovery has experienced slow progress in large part due to the experimental difficulty in evaluating their interaction with novel compounds. Genome-wide association studies continue to identify ion channel mutations that result in ion channel irregularities, which contribute to many debilitating diseases including Parkinson's, Alzheimer's, hyperactivity disorders, epilepsy, and autism. The constantly increasing rate of discovery of new candidate targets necessitates high-throughput techniques to evaluate their efficacy as therapeutic targets.

The need for high-throughput ion channel screening has spurred the development of several methods based on indirect measurement of ion channel activity, such as ion-flux assays and cell-based assays with membrane potential- or $Ca^{2+}$-sensitive dyes. Although these methods have become an integral part of ion channel drug discovery efforts, electrophysiological measurements that directly monitor the electric activity of ion channels remain the benchmark assay for confirmation of compound activity and efficacy. However, electrophysiological measurements have been of limited utility in drug screening efforts in large part due to their labor-intensive and low-throughput nature. To address this drawback, automated planar-patch electrophysiology platforms have been developed, allowing for higher throughput drug screening experiments. Although planar-patch platforms have proven useful in several drug discovery programs including identification and optimization efforts, their application is limited to large cells and stable cell lines designed to express the channel of interest. However, the process of stably expressing cell lines is costly, time-consuming, and often associated with low viability. In addition, characterization of the compound's activity in dissociated cells does not warrant the same effect in a complex neuronal network. Automated planar-patch platforms are limited not only by their poor performance with primary mammalian neurons and neuronal cultures, but also by their unsuitability of recording from connected pairs of neurons.

Nanowires (NWs) provide a powerful new system for determining electrical conditions within cells, or applying electrical forces to cells. However, due to their size, typically on the order of nanometers, it is difficult to expose arrays of nanowires and cells to different conditions. Accordingly, improvements are needed.

SUMMARY

The present invention generally relates to nanowires. The subject matter of the present invention involves, in some cases, interrelated products, alternative solutions to a particular problem, and/or a plurality of different uses of one or more systems and/or articles.

In one aspect, the present invention is generally directed to an article. In one set of embodiments, the article includes a plurality of upstanding nanowires on a substrate, in electrical communication with an integrated circuit.

The invention, in another aspect, is generally directed to a method. In one set of embodiments, the method includes inserting one or more nanowires into a cell. In some cases, the one or more nanowires may be upstanding nanowires on a substrate and/or are in electrical communication with an integrated circuit.

The method, in another set of embodiments, includes applying electroporation and/or voltage to a cell using one or more nanowires inserted into a cell. In some cases, the one or more nanowires may be upstanding nanowires on a substrate and/or are in electrical communication with an integrated circuit.

The method, in another set of embodiments, includes exposing a plurality of cells to one or more compounds. In some cases, at least some of the cells are penetrated with one or more nanowires. In some cases, the one or more nanowires may be upstanding nanowires on a substrate and/or are in electrical communication with an integrated circuit.

In another aspect, the present invention encompasses methods of making one or more of the embodiments described herein. In one set of embodiments, the method includes depositing a nanowire-material-comprising layer on an integrated circuit. In some cases, the method further includes generating an etch mask. In some cases, the method further includes etching the nanowire-material-comprising layer to form one or more nanowires. In some embodiments, the method further includes depositing a conformal coating comprising an electrically conductive material on the one or more nanowires.

In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to nanowires. In one aspect, the present invention is generally directed to systems and methods of individually addressing nanowires on a surface, e.g., that are substantially upstanding or vertically-oriented with respect to the surface. In some cases, one or more nanowires may be individually addressed using various integrated circuit ("IC") technologies, such as CMOS. For example, the nanowires may form an array on top of an active CMOS integrated circuit.

Figure 1:
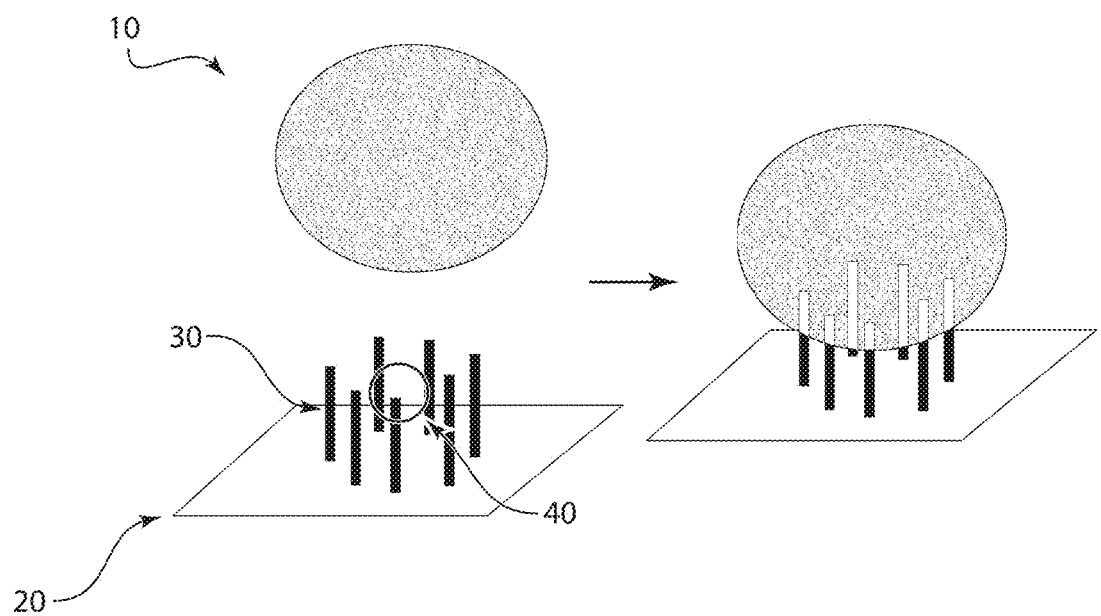
FIG. 1 is a schematic of a molecular delivery process using an embodiment of the invention.

One aspect of the invention relates to nanowires positioned in contact with a cell, e.g., as is shown in FIG. 1, where a cell 10 is brought into contact with a substrate 20 having an array of vertical nanowires 30. The substrate may be planar or substantially planar in some embodiments. One or more of the ends 40 of nanowires 30 may be inserted into cell 10. As discussed herein, some or all of the nanowires may be individually addressable, e.g., for recording and/or for applying an electrical force to the cell. Nanowires that may be used can be formed of material with low cytotoxicity, such as silicon, silicon oxide, silicon nitride, silicon carbide, iron oxide, aluminum oxide, iridium oxide, tungsten, stainless steel, silver, platinum, and gold. Further examples are discussed below.

Thus, certain aspects of the invention are generally directed to one or more nanowires on a substrate. The nanowires may be upstanding or substantially oriented vertically, with respect to the surface. For example, on average, the upstanding nanowires may form an angle with respect to a substrate of between about 80° and about 100°, between about 85° and about 95°, or between about 88° and about 92°. In some cases, the average angle is about 90°. As used herein, the term "nanowire" (or "NW") refers to a material in the shape of a wire or rod having a diameter in the range of 1 nm to 1 micrometer (μm). The NWs may be formed from materials with low cytotoxicity; suitable materials include, but are not limited to, silicon, silicon oxide (e.g., silicon dioxide), silicon nitride, silicon carbide, iron oxide, aluminum oxide, iridium oxide, tungsten, stainless steel, silver, platinum, and gold. Other suitable materials include aluminum, copper, molybdenum, tantalum, titanium, nickel, tungsten, chromium, or palladium. In some embodiments, the nanowire comprises or consists essentially of a semiconductor. Typically, a semiconductor is an element having semiconductive or semi-metallic properties (i.e., between metallic and non-metallic properties). An example of a semiconductor is silicon. Other non-limiting examples include elemental semiconductors, such as gallium, germanium, diamond (carbon), tin, selenium, tellurium, boron, or phosphorous. In other embodiments, more than one element may be present in the nanowires as the semiconductor, for example, gallium arsenide, gallium nitride, indium phosphide, cadmium selenide, etc.

The size and density of the NWs in the NW arrays may be varied; the lengths, diameters, and density of the NWs can be configured to permit adhesion and penetration of cells. In some embodiments, the length of the NWs can be 0.1-10 micrometers (μm). In some cases, the diameter of the NWs can be 50-300 nm. In certain embodiments, the aspect ratio (e.g., length to diameter) of the NWs can be about 3:1 to about 500:1. In certain embodiments, the density of the NWs can be 0.05-5 NWs per micrometer (μm$^2$). Other examples are discussed below.

The nanowires may have any suitable length, as measured moving away from the substrate. The nanowires may have substantially the same lengths, or different lengths in some cases. For example, the nanowires may have an average length of at least about 0.1 micrometers, at least about 0.2 micrometers, at least about 0.3 micrometers, at least about 0.5 micrometers, at least about 0.7 micrometers, at least about 1 micrometer, at least about 2 micrometers, at least about 3 micrometers, at least about 5 micrometers, at least about 7 micrometers, or at least about 10 micrometers. In some cases, the nanowires may have an average length of no more than about 10 micrometers, no more than about 7 micrometers, no more than about 5 micrometers, no more than about 3 micrometers, no more than about 2 micrometers, no more than about 1 micrometer, no more than about 0.7 micrometers, no more than about 0.5 micrometers, no more than about 0.3 micrometers, no more than about 0.2 micrometers, or no more than about 0.1 micrometers. Combinations of any of these are also possible in some embodiments.

The nanowires may also have any suitable diameter, or narrowest dimension if the nanowires are not circular. The nanowires may have substantially the same diameters, or in some cases, the nanowires may have different diameters. In some cases, the nanowires may have an average diameter of at least about 10 nm, at least about 30 nm, at least about 50 nm, at least about 70 nm, at least about 100 nm, at least about 200 nm, at least about 300 nm, etc., and/or the nanowires may have an average diameter of no more than about 300 nm, no more than about 200 nm, no more than about 100 nm, no more than about 70 nm, no more than about 50 nm, no more than about 30 nm, no more than about 20 nm, or no more than about 10 nm, or any combination of these.

In addition, in some cases, the density of nanowires on the substrate, or on a region of the substrate defined by nanowires, may be at least about 0.01 nanowires per square micrometer, at least about 0.02 nanowires per square micrometer, at least about 0.03 nanowires per square micrometer, at least about 0.05 nanowires per square micrometer, at least about 0.07 nanowires per square micrometer, at least about 0.1 nanowires per square micrometer, at least about 0.2 nanowires per square micrometer, at least about 0.3 nanowires per square micrometer, at least about 0.5 nanowires per square micrometer, at least about 0.7 nanowires per square micrometer, at least about 1 nanowire per square micrometer, at least about 2 nanowires per square micrometer, at least about 3 nanowires per square micrometer, at least about 4 nanowires per square micrometer, at least about 5 nanowires per square micrometer, etc. In addition, in some embodiments, the density of nanowires on the substrate may be no more than about 10 nanowires per square micrometer, no more than about 5 nanowires per square micrometer, no more than about 4 nanowires per square micrometer, no more than about 3 nanowires per square micrometer, no more than about 2 nanowires per square micrometer, no more than about 1 nanowire per square micrometer, no more than about 0.7 nanowires per square micrometer, no more than about 0.5 nanowires per square micrometer, no more than about 0.3 nanowires per square micrometer, no more than about 0.2 nanowires per square micrometer, no more than about 0.1 nanowires per square micrometer, no more than about 0.07 nanowires per square micrometer, no more than about 0.05 nanowires per square micrometer, no more than about 0.03 nanowires per square micrometer, no more than about 0.02 nanowires per square micrometer, or no more than about 0.01 nanowires per square micrometer.

The nanowires may be regularly or irregularly spaced on the substrate. For example, the nanowires may be positioned within a rectangular grid with periodic spacing, e.g., having a periodic spacing of at least about 0.01 micrometers, at least about 0.03 micrometers, at least about 0.05 micrometers, at least about 0.1 micrometers, at least about 0.3 micrometers, at least about 0.5 micrometers, at least about 1 micrometer, at least about 2 micrometers, at least about 3 micrometers, at least about 5 micrometers, at least about 10 micrometers, etc. In some cases, the periodic spacing may be no more than about 10 micrometers, no more than about 5 micrometers, no more than about 3 micrometers, no more than about 1 micrometer, no more than about 0.5 micrometers, no more than about 0.3 micrometers, no more than about 0.1 micrometers, no more than about 0.05 micrometers, no more than about 0.03 micrometers, no more than about 0.01 micrometers, etc. Combinations of these are also possible, e.g., the array may have a periodic spacing of nanowires of between about 0.01 micrometers and about 0.03 micrometers.

In some cases, the nanowires (whether regularly or irregularly spaced) may be positioned on the substrate such that the average distance between a nanowire and its nearest neighboring nanowire is at least about 0.01 micrometers, at least about 0.03 micrometers, at least about 0.05 micrometers, at least about 0.1 micrometers, at least about 0.3 micrometers, at least about 0.5 micrometers, at least about 1 micrometer, at least about 2 micrometers, at least about 3 micrometers, at least about 5 micrometers, at least about 10 micrometers, etc. In some cases, the distance may be no more than about 10 micrometers, no more than about 5 micrometers, no more than about 3 micrometers, no more than about 1 micrometer, no more than about 0.5 micrometers, no more than about 0.3 micrometers, no more than about 0.1 micrometers, no more than about 0.05 micrometers, no more than about 0.03 micrometers, no more than about 0.01 micrometers, etc. In some cases, the average distance may fall within any of these values, e.g., between about 0.5 micrometers and about 2 micrometers.

In certain aspects, the substrate may comprise more than one region of nanowires, e.g., patterned as discussed herein. For example, a pre-determined pattern of photons or electrons may be used to produce a substrate comprising a first region of nanowires and a second region of nanowires. In addition, in some cases, more than two such regions of nanowires may be produced on a substrate. For example, there may be at least 3, at least 6, at least 10, at least 15, at least 20, at least 50, or at least 100 separate regions of nanowires on a substrate. In some cases, the regions are separate from each other. Any number of nanowires may be present in a region, e.g., at least about 10, at least about 20, at least about 50, at least about 100, at least about 300, at least about 1000, etc. The nanowires may be present in any suitable configuration or array, e.g., in a rectangular or a square array.

The nanowires in a first region and a second region may be the same, or there may be one or more different characteristics between the nanowires. For example, the nanowires in the first region and the second region may have different average diameters, lengths, densities, biological effectors, or the like. If more than two regions of nanowires are present on the substrate, each of the regions may independently be the same or different.

The substrate may be formed of the same or different materials as the nanowires. For example, the substrate may comprise silicon, silicon oxide, silicon nitride, silicon carbide, iron oxide, aluminum oxide, iridium oxide, tungsten, stainless steel, silver, platinum, gold, gallium, germanium, or any other materials described herein that a nanowire may be formed from. In one embodiment, the substrate is formed from a semiconductor. In some cases, the substrate may include CMOS or other technologies, e.g., as discussed herein.

In some embodiments, arrays of NWs on a substrate may be obtained by growing NWs from a precursor material. As a non-limiting example, chemical vapor deposition (CVD) may be used to grow NWs by placing or patterning catalyst or seed particles (typically with a diameter of 1 nm to a few hundred nm) atop a substrate and adding a precursor to the catalyst or seed particles. When the particles become saturated with the precursor, NWs can begin to grow in a shape that minimizes the system's energy. By varying the precursor, substrate, catalyst/seed particles (e.g., size, density, and deposition method on the substrate), and growth conditions, NWs can be made in a variety of materials, sizes, and shapes, at sites of choice.

In certain embodiments, arrays of NWs on a substrate may be obtained by growing NWs using a top-down process that involves removing predefined structures from a supporting substrate. As a non-limiting example, the sites where NWs are to be formed may be patterned into a soft mask and subsequently etched to develop the patterned sites into three-dimensional nanowires. Methods for patterning the soft mask include, but are not limited to, photolithography and electron beam lithography. The etching step may be either wet or dry.

As mentioned, in some aspects, one or more nanowires may be individually or uniquely addressable, e.g., using an integrated circuit. Those of ordinary skill in the art will be aware of techniques for fabricating and using a variety of integrated circuits. Integrated circuit ("IC") may use a variety of semiconductor materials (e.g., silicon (Si), silicon germanium (SiGe), gallium arsenide (GaAs), indium phosphide (InP), etc.) to implement electronic components and circuits. For example, one example of IC technology is "CMOS" (Complimentary-Metal-Oxide-Semiconductor) technology, with which silicon integrated circuits are fabricated. For instance, one example implementation of such an IC chip may be fabricated using standard CMOS protocols. It should be appreciated, however, that the present disclosure is not intended to be limiting in this respect, as other semiconductor-based technologies may be utilized to implement various embodiments of the microelectronics portion of the systems discussed herein. Other electronic components may be added as well, in various embodiments of the invention.

In some embodiments, the integrated circuit comprises one or more connection sites. The connection site may be a site comprising an electrically conductive surface (e.g., to facilitate electrical connection to one or more other structures, such as one or more nanowires) in electrical communication with one or more electronic components (e.g., an amplifier unit, a stimulator unit). In some embodiments, the integrated circuit comprises at least about 1, at least about 4, at least about 5, at least about 9, at least about 10, at least about 25, at least about 100, at least about 225, at least about 400, at least about 625, at least about 1000, at least about 1024, at least about 2000, at least about 5000, at least about 10,000, at least about 16,384, at least about 20,000, at least about 50,000, at least about 100,000, at least about 150,000, at least about 200,000, at least about 250,000, at least about 300,000, at least about 400,000, or at least about 500,000 connection sites. In some cases, at least one connection site is in electrical communication with at least about 1, at least about 4, at least about 5, at least about 9, at least about 10, at least about 25, at least about 100, at least about 225, at least about 400, at least about 625, at least about 1000, at least about 1024, at least about 2000, at least about 5000, or at least about 10,000 nanowires. The integrated circuit may, in certain cases, be in electrical communication with at least about 1, at least about 4, at least about 5, at least about 9, at least about 10, at least about 25, at least about 100, at least about 225, at least about 400, at least about 625, at least about 1000, at least about 1024, at least about 2000, at least about 5000, at least about 10,000, at least about 16,384, at least about 20,000, at least about 50,000, at least about 100,000, at least about 150,000, at least about 200,000, at least about 250,000, at least about 300,000, at least about 400,000, at least about 500,000, or at least about 1,000,000 nanowires.

In some embodiments, a connection site comprises an electrically conductive surface. The electrically conductive surface may comprise a metal (e.g., a metal pad). Non-limiting examples of suitable metals include aluminum, titanium, platinum, copper, gold, and/or chromium.

According to some embodiments, a connection site is in electrical communication with one or more amplifier units. An amplifier unit generally refers to an electronic component that receives an electrical signal (e.g., an electrical signal from a biological cell) and amplifies the signal (e.g., increases the voltage and/or current of the signal). In some cases, the amplifier unit has relatively high gain (e.g., voltage gain). In certain embodiments, the voltage gain of an electrical signal (e.g., output voltage divided by input voltage) is at least about 0.1 V/V, at least about 0.5 V/V, at least about 1 V/V, at least about 5 V/V, at least about 10 V/V, at least about 20 V/V, at least about 50 V/V, at least about 80 V/V, at least about 100 V/V, at least about 120 V/V, at least about 150 V/V, at least about 200 V/V, at least about 300 V/V, at least about 400 V/V, at least about 500 V/V, at least about 600 V/V, at least about 700 V/V, at least about 800 V/V, at least about 900 V/V, or at least about 1000 V/V, etc. In some cases, the presence of one or more amplifier units at a connection site in an integrated circuit may advantageously mitigate the effects of relatively high nanowire impedance and/or relatively low signal amplitude and/or frequency.

In some embodiments, at least a portion of the connection sites in an integrated circuit are individually in electrical communication with an amplifier unit. In certain cases, each connection site is individually in electrical communication with an amplifier unit, although in other cases, a connection site may be in electrical communication with more than one amplifier unit, or an amplifier may be in electrical communication with more than one connection site. In some cases, an integrated circuit comprises at least about 1, at least about 4, at least about 5, at least about 9, at least about 10, at least about 25, at least about 100, at least about 225, at least about 400, at least about 625, at least about 1000, at least about 1024, at least about 2000, at least about 5000, at least about 10,000, at least about 16,384, at least about 20,000, at least about 50,000, at least about 100,000, at least about 150,000, at least about 200,000, at least about 250,000, at least about 300,000, at least about 400,000, or at least about 500,000 amplifier units. In some embodiments, one or more nanowires are in electrical communication with an amplifier unit of a connection site.

In some cases, the amplifier unit is AC coupled (e.g., capacitively coupled) to one or more nanowires. In certain cases, AC coupling may advantageously filter out DC components and reduce noise. Accordingly, in some embodiments, the amplifier unit comprises one or more capacitors in series with one or more nanowires. In certain cases, the amplifier unit comprises an input variable capacitance array, which may match the capacitance of one or more nanowires in electrical communication with the amplifier unit.

The amplifier unit may comprise any amplifier known in the art. In certain embodiments, an amplifier unit comprises a low noise amplifier (LNA) (e.g., a single-ended low noise amplifier) and/or a variable gain amplifier (VGA). For example, an amplifier unit may comprise an LNA electrically coupled to a VGA. In some cases, an amplifier unit comprises one or more transistors (e.g., bipolar junction transistors and/or metal oxide semiconductor field-effect transistors (MOSFETs)). The amplifier unit may, in some embodiments, comprise 200 or fewer transistors, 150 or fewer transistors, 100 or fewer transistors, 75 or fewer transistors, 50 or fewer transistors, 40 or fewer transistors, 30 or fewer transistors, 20 or fewer transistors, 15 or fewer transistors, 10 or fewer transistors, 5 or fewer transistors, 2 or fewer transistors, or 1 transistor. In some cases, it may be advantageous for an amplifier circuit to comprise relatively few transistors in order to reduce power consumption, which may be desirable to prevent damage to biological cells.

In certain embodiments, an amplifier circuit is in electrical communication with one or more filters (e.g., frequency filters). In some embodiments, the filter is a high-pass filter (e.g., a filter that passes signals having a frequency above a certain cut-off value), a low-pass filter (e.g., a filter that passes signals having a frequency below a certain cut-off value), or a bandpass filter (e.g., a filter that passes signals having a frequency above a first cut-off value and below a second cut-off value). The filter may, for example, be positioned in a negative feedback path of the amplifier unit. In certain cases, the filter may advantageously filter out 1/f noise. In some embodiments, the filter has a high frequency pole of at least about 1 kHz, at least about 5 kHz, at least about 10 kHz, or at least about 20 kHz. The filter may, in some embodiments, have a low frequency pole of about 1 Hz or less, about 0.5 Hz or less, about 0.2 Hz or less, about 0.1 Hz or less, about 0.05 Hz or less, about 0.02 Hz or less, or about 0.01 Hz or less. In some embodiments, the filter comprises a pseudo resistor comprising one or more diodes. A non-limiting example of a suitable type of diode is a PN junction diode (e.g., a PN junction silicon diode). In some cases, the pseudo resistor comprises 10 or fewer diodes, 7 or fewer diodes, 5 or fewer diodes, or 3 or fewer diodes. In certain embodiments, the pseudo resistor has a resistance of least about 1 teraohm, at least about 2 teraohms, at least about 5 teraohms, at least about 10 teraohms, at least about 50 teraohms, or at least about 100 teraohms. The pseudo resistor may, in some cases, be in parallel with one or more capacitors (e.g., one or more poly-insulator-poly capacitors). In some cases, the one or more capacitors have a capacitance of at least about 1 femtofarad, at least about 2 femtofarads, at least about 5 femtofarads, at least about 10 femtofarads, at least about 50 femtofarads, or at least about 100 femtofarads.

According to some embodiments, a connection site is in electrical communication with one or more stimulator units. A stimulator unit may be an electronic component that can apply an electrical stimulus (e.g., a voltage pulse) to another electronic component or other structure. In some embodiments, a stimulator unit comprises a plurality of voltage stimulus sources. For example, a stimulator unit may comprise at least about 1, at least about 2, at least about 3, at least about 4, at least about 5, or at least about 10 voltage stimulus sources. Any type of voltage stimulus source known in the art may be used. In some cases, the voltage stimulus source may be capable of providing a signal having a voltage of at least about 1 V, at least about 2 V, at least about 3 V, at least about 4 V, at least about 5 V, at least about 10 V, at least about 15 V, at least about 20 V, at least about 25 V, or at least about 30 V, etc. In some cases, the stimulator unit may further comprise a multiplexer in electrical communication with the plurality of voltage stimulus sources. The multiplexer may be a device that selects and forwards an electrical signal (e.g., stimulation signal) from one of the plurality of voltage stimulus sources. The presence of one or more stimulator units at a connection site in an integrated circuit may advantageously allow stimulation of one or more biological cells (e.g., via one or more nanowires).

In some embodiments, at least a portion of the connection sites in an integrated circuit are individually in electrical communication with a stimulator unit. In certain cases, each connection site is individually in electrical communication with a stimulator unit. In some cases, an integrated circuit comprises at least about 1, at least about 4, at least about 5, at least about 9, at least about 10, at least about 25, at least about 100, at least about 225, at least about 400, at least about 625, at least about 1000, at least about 1024, at least about 2000, at least about 5000, at least about 10,000, at least about 16,384, at least about 20,000, at least about 50,000, at least about 100,000, at least about 150,000, at least about 200,000, at least about 250,000, at least about 300,000, at least about 400,000, or at least about 500,000 stimulator units. In some embodiments, one or more nanowires are in electrical communication with a stimulator unit of a connection site.

In some embodiments, a connection site is in electronic communication with a local digital memory (e.g., an electronic data storage device). In some embodiments, the local digital memory has a capacity of at least about 2 bits, at least about 4 bits, at least about 8 bits, at least about 16 bits, at least about 32 bits, at least about 64 bits, at least about 128 bits, at least about 256 bits, or at least about 512 bits or more. According to some embodiments, the digital memory is electronically connected to a stimulator unit of the connection site. In certain cases, the digital memory may control the amplitude and/or frequency of an applied electrical stimulus. For example, the digital memory may select the voltage stimulus source of the stimulator unit to apply the electrical stimulus. In some embodiments, the digital memory is electronically connected to an amplifier unit of the connection site. In certain cases, the digital memory may control the variable gain of the amplifier unit. In some embodiments, the digital memory may turn at least a portion of the amplifier unit and/or at least a portion of the stimulator unit on or off. In some cases, the ability of the digital memory to turn the amplifier unit and/or stimulator unit on or off may advantageously result in low power consumption, which may be desirable to prevent damage to biological cells.

In some embodiments, the integrated circuit comprises an output multiplexer (e.g., an analog multiplexer). The output multiplexer may advantageously allow for simultaneous recording from a plurality of connection sites. In some embodiments, the output multiplexer may sample the integrated circuit at a sufficiently high frequency to resolve electrical signals from biological cells. For example, the output multiplexer may sample the integrated circuit chip at a sample of frequency of at least about 1 kHz, at least about 5 kHz, at least about 10 kHz, at least about 20 kHz, at least about 50 kHz, or at least about 100 kHz.

In some embodiments, one or more nanowires may be in electrical communication with a connection site of the integrated circuit. The one or more nanowires may be, in some embodiments, in physical contact (e.g., direct physical contact) with a connection site. For example, at least a portion of a nanowire may be in direct physical contact with the electrically conductive surface (e.g., metal pad) of a connection site. In some embodiments, one or more intervening layers may be positioned between a nanowire and a connection site. The one or more intervening layers may, in some cases, be substantially electrically conductive. In some cases, it may be advantageous for the one or more nanowires to be in physical contact with the connection site to reduce noise and/or reduce attenuation of signals transmitted between the nanowires and one or more electronic components connected to the connection site. For example, positioning the nanowires in physical contact with the connection site may avoid a relatively long signal path to off-chip electronics, which may have large stray capacitance and lead to deleterious signal attenuation.

In some embodiments, the integrated circuit is capable of measuring signals having a relatively low amplitude. In some cases, the integrated circuit measures signals having an amplitude of about 500 mV or less, about 200 mV or less, about 100 mV or less, about 50 mV or less, about 20 mV or less, about 10 mV or less, about 5 mV or less, about 4 mV or less, about 3 mV or less, about 2 mV or less, about 1 mV or less, about 500 µV or less, about 200 µV or less, about 100 µV or less, about 50 µV or less, about 20 µV or less, or about 10 µV or less.

In some embodiments, the integrated circuit is capable of measuring signals having a relatively low frequency. In some embodiments, the integrated circuit measures signals having a frequency of about 500 kHz or less, about 200 kHz or less, about 100 kHz or less, about 50 kHz or less, about 20 kHz or less, about 10 kHz or less, about 5 kHz or less, about 2 kHz or less, about 1 kHz or less, about 500 Hz or less, about 200 Hz or less, about 100 Hz or less, about 50 Hz or less, about 20 Hz or less, about 10 Hz or less, about 5 Hz or less, about 2 Hz or less, about 1 Hz or less, about 0.5 Hz or less, about 0.2 Hz or less, or about 0.1 Hz or less.

According to some embodiments, the integrated circuit may consume a relatively low amount of power. In some cases, it may be advantageous for the integrated circuit to consume relatively little power to minimize heat dissipation and prevent damage to biological cells. In some embodiments, the integrated circuit consumes about 1 W or less, about 0.5 W or less, about 0.2 W or less, about 0.1 W or less, about 0.05 W or less, about 0.02 W or less, about 0.01 W or less, about 0.005 W or less, about 0.002 W or less, or about 0.001 W or less.

Figure 2:
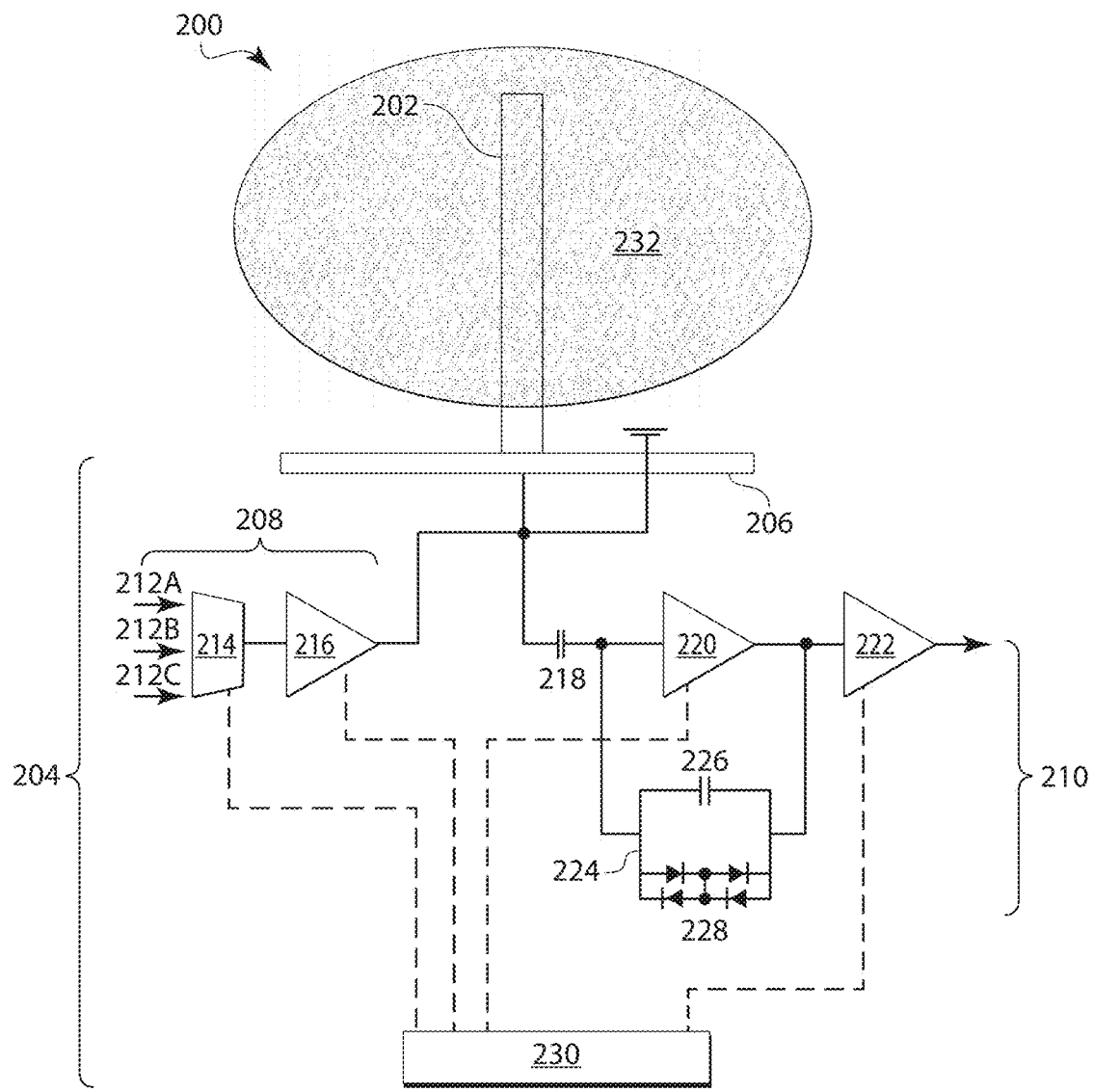
FIG. 2 is a schematic of a nanowire in electrical communication with a biological cell and a connection site of an integrated circuit (not to scale), according to some embodiments.

A schematic diagram of an exemplary system 200 comprising a nanowire 202 and a connection site 204 of an integrated circuit, according to some embodiments, is shown in FIG. 2. In system 200, connection site 204 comprises metal pad 206, which is in direct physical contact with nanowire 202. Metal pad 206 is in electrical communication with stimulator unit 208 and amplifier unit 210. As shown in FIG. 2, stimulator unit 208 comprises voltage stimulus sources 212A, 212B, and 212C, multiplexer 214, and stimulator 216. Amplifier unit 210 comprises input capacitor 218, low-noise amplifier (LNA) 220, variable gain amplifier (VGA) 222, and high-pass filter 224. High-pass filter 224 comprises capacitor 226 in parallel with pseudo resistor 228, where pseudo resistor 228 comprises a plurality of feedback diodes. Connection site 204 also comprises local digital memory 230, which is electronically connected to multiplexer 214 and stimulator 216 of stimulator unit 208 and LNA 220 and VGA 222 of amplifier unit 210. Nanowire 202 may be inserted in biological cell 232.

In operation, connection site 204 may be configured to apply an electrical stimulus (e.g., a voltage pulse) to biological cell 232. Accordingly, digital memory 230 may send signals to enable multiplexer 214 and stimulator 216 of stimulator unit 208 and disable LNA 220 and VGA 222 of amplifier unit 210. Digital memory 230 may also send a signal to multiplexer 214 selecting which of voltage stimulus sources 212A, 212B, and 212C to use to apply a stimulation signal. The stimulation signal may be transmitted from the selected voltage stimulus source of stimulator unit 208 to metal pad 206 and nanowire 202. The stimulation signal may then be transmitted from nanowire 202 to biological cell 232. In some cases, the stimulation signal may induce an effect in biological cell 232.

In some cases, connection site 204 may be configured to record an electrical signal from biological cell 232. Accordingly, digital memory 230 may send signals to disable multiplexer 214 and stimulator 216 of stimulator unit 208 and enable LNA 220 and VGA 222 of amplifier unit 210. Digital memory 230 may also control the gain of VGA 222. An electrical signal (e.g., a post-synaptic potential, an action potential) from biological cell 232 may be transmitted to nanowire 202 and, subsequently, to metal pad 206 and amplifier unit 210. In amplifier unit 210, the biological signal may be transmitted through input capacitor 218 to LNA 220, which may increase the voltage of the biological signal. High-pass filter 224 may remove noise having a frequency below a certain cut-off value. The amplified signal may then be transmitted to VGA 222 to be further amplified, with the gain controlled by digital memory 230. The further amplified signal may then be transmitted to an output multiplexer (not shown).

In one aspect, the nanowires may be contained within a plurality of wells, e.g., containing cells. In some cases, the cells may be studied in parallel fashion, e.g., to test a variety of drugs or potential drug candidates, to study the effect of one or more compositions or agents on one or more cells or cell types, or the like. For example, in some cases, the wells may be arranged as in multiwell plates, which may be of any size.

However, in certain embodiments, the wells are arranged as in the dimensions of a microwell plate, e.g., having standard dimensions (about 5 inches×about 3.33 inches, or about 128 mm×86 mm) and/or standard numbers of wells therein. For example, there may be 6, 24, 48, 96, 384, 1536 or 3456 wells present. In some cases, the device may include multiwell plates, which may be fabricated from any suitable material, e.g., polystyrene, polypropylene, polycarbonate, cyclo-olefins, or the like. Microwell plates can be made by injection molding, casting, machining, laser cutting, or vacuum sheet forming one or more resins, and can be made from transparent or opaque materials. Many such microwell plates are commercially available.

In one set of embodiments, the multiwell plate is prepared by immobilizing a bottomless multiwell plate with a substrate comprising a plurality of upstanding nanowires. For example, the bottomless multiwell plate may be a commercially available bottomless microwell plate, e.g., a bottomless 384-well microwell plate. The substrate and the nanowires may comprise semiconductor materials such as silicon, or other materials as described herein.

In some embodiments, the multiwell plate and the substrate may be immobilized with respect to each other by the use of a suitable adhesive. Non-limiting examples of adhesives include acrylic adhesives, pressure-sensitive adhesives, silicone adhesives (e.g., UV curable silicones or RTV silicones), biocompatible adhesives, epoxies, or the like. Non-limiting examples of biocompatible glues include, but are not limited to, Master Bond EP42HT-2ND-2MED BLACK and Master Bond EP42HT-2 CLEAR (Master Bond). The adhesive, in some cases, may be a permanent adhesive. Many such adhesives can be obtained commercially from companies such as 3M, Loctite, or Adhesives Research.

The multiwell plate and the substrate may be directly immobilized to each other, and/or there may be other materials positioned between the multiwell plate and the substrate, for example, one or more gaskets (e.g., comprising silicone, rubber, neoprene, nitrile rubber, fiberglass, polytetrafluoroethylene, etc.). In some cases, these materials may be dimensioned and arranged to be in the same pattern as the wells (or a subset thereof) of the multiwell plate to which they are being attached.

In one aspect, at least some of the NWs may be used to deliver a molecule of interest into a cell, e.g., through insertion of a NW into the cell. In certain embodiments of the invention, at least some of the NWs may undergo surface modification so that molecules of interest can be attached to them. It should be appreciated that the NWs can be complexed with various molecules according to any method known in the art. It should also be appreciated that the molecules connected to different NWs may be distinct. In some embodiments, a NW may be attached to a molecule of interest through a linker. The interaction between the linker and the NW may be covalent, electrostatic, photosensitive, or hydrolysable. As a specific non-limiting example, a silane compound may be applied to a NW with a surface layer of silicon oxide, resulting in a covalent SiO bond. As another specific non-limiting example, a thiol compound may be applied to a NW with a surface layer of gold, resulting in a covalent Au—S bond. Examples of compounds for surface modification include, but are not limited to, aminosilanes such as (3-aminopropyl)-trimethoxysilane, (3-aminopropyl)-triethoxysilane, 3-(2-aminoethylamino)propyl-dimethoxymethylsilane, (3-aminopropyl)-diethoxy-methylsilane, [3-(2-aminoethylamino)propyl]trimethoxysilane, bis [3-(trimethoxysilyl)propyl]amine, and (11-aminoundecyl)-triethoxysilane; glycidoxysilanes such as 3-glycidoxypropyldimethylethoxysilane and 3-glycidyloxypropyl) trimethoxysilane; mercaptosilanes such as (3-mercaptopropyl)-trimethoxysilane and (11-mercaptoundecyl)-trimethoxysilane; and other silanes such as trimethoxy(octyl)silane, trichloro(propyl)silane, trimethoxyphenylsilane, trimethoxy(2-phenylethyl)silane, allyltriethoxysilane, allyltrimethoxysilane, 3-[bis(2-hydroxyethyl)amino]propyl-triethoxysilane, 3-(trichlorosilyl) propyl methacrylate, and (3-bromopropyl)trimethoxysilane. Other non-limiting examples of compounds that may be used to form the linker include poly-lysine, collagen, fibronectin, and laminin.

In addition, in various embodiments, a nanowire may be prepared for binding or coating of a suitable biological effector by activating the surface of the nanowire, silanizing at least a portion of the nanowire, and reacting a crosslinker to the silanized portions of the nanowire. Methods for activating the surface include, but are not limited to, surface oxidation, such as by plasma oxidation or acid oxidation. Non-limiting examples of suitable types of crosslinkers that are commercially available and known in the art include maleimides, histidines, haloacetyls, and pyridyldithiols.

Similarly, the interaction between the linker and the molecule to be delivered can be covalent, electrostatic, photosensitive, or hydrolysable. In some embodiments, a molecule of interest attached to or coated on a NW may be a biological effector. As used herein, a "biological effector" refers to a substance that is able to modulate the expression or activity of a cellular target. It includes, but is not limited to, a small molecule, a protein (e.g., a natural protein or a fusion protein), an enzyme, an antibody (e.g., a monoclonal antibody), a nucleic acid (e.g., DNA, including linear and plasmid DNAs; RNA, including mRNA, siRNA, and microRNA), and a carbohydrate. The term "small molecule" refers to any molecule with a molecular weight below 1000 Da. Non-limiting examples of molecules that may be considered to be small molecules include synthetic compounds, drug molecules, oligosaccharides, oligonucleotides, and peptides. The term "cellular target" refers to any component of a cell. Non-limiting examples of cellular targets include DNA, RNA, a protein, an organelle, a lipid, or the cytoskeleton of a cell. Other examples include the lysosome, mitochondria, ribosome, nucleus, or the cell membrane.

In some cases, the nanowires can be used to deliver biological effectors or other suitable biomolecular cargo into a population of cells at surprisingly high efficiencies. Furthermore, such efficiencies may be achieved regardless of cell type, as the primary mode of interaction between the nanowires and the cells is physical insertion, rather than biochemical interactions (e.g., as would appear in traditional pathways such as phagocytosis, receptor-mediated endocytosis, etc.). For instance, in a population of cells on the surface of the substrate, at least about 50%, at least about 60%, at least about 70%, at least about 80%, or at least about 90% of the cells may have at least one nanowire inserted therein. In some cases, as discussed herein, the nanowires may have at least partially coated thereon one or more biological effectors. Thus, in some embodiments, biological effectors may be delivered to at least about 50%, at least about 60%, at least about 70%, at least about 80%, or at least about 90% of the cells on the substrate, e.g., via the nanowires.

In one set of embodiments, the surface of the substrate may be treated in any fashion that allows binding of cells to occur thereto. For example, the surface may be ionized and/or coated with any of a wide variety of hydrophilic and/or cytophilic materials, for example, materials having exposed carboxylic acid, alcohol, and/or amino groups. In another set of embodiments, the surface of the substrate may be reacted in such a manner as to produce carboxylic acid, alcohol, and/or amino groups on the surface. In some cases, the surface of the substrate may be coated with a biological material that promotes adhesion or binding of cells, for example, materials such as fibronectin, laminin, vitronectin, albumin, collagen, or peptides or proteins containing RGD sequences.

It should be understood that for a cell to adhere to the nanowire, a separate chemical or "glue" is not necessarily required. In some cases, sufficient nanowires may be inserted into a cell such that the cell cannot easily be removed from the nanowires (e.g., through random or ambient vibrations), and thus, the nanowires are able to remain inserted into the cells. In some cases, the cells cannot be readily removed via application of an external fluid after the nanowires have been inserted into the cells.

In some cases, merely placing or plating the cells on the nanowires is sufficient to cause at least some of the nanowires to be inserted into the cells. For example, a population of cells suspended in media may be added to the surface of the substrate containing the nanowires, and as the cells settle from being suspended in the media to the surface of the substrate, at least some of the cells may encounter nanowires, which may (at least in some cases) become inserted into the cells.

Any suitable type of cell may be studied. For example, the cell may be a prokaryotic cell or a eukaryotic cell. The cell may be from a single-celled organism or a multi-celled organism. In some cases, the cell is genetically engineered, e.g., the cell may be a chimeric cell. The cell may be bacteria, fungi, a plant cell, an animal cell, etc. The cell may be from a human or a non-human animal or mammal (e.g., mouse, rat, pig, etc.). For instance, if the cell is from an animal, the cell may be a cardiac cell, a fibroblast, a keratinocyte, a hepatocyte, a chondrocyte, a neural cell (e.g., a cortical neuron, an olfactory receptor neuron, an olfactory sensory neuron), an osteocyte, an osteoblast, a muscle cell (e.g., a cardiomyocyte), a blood cell, an endothelial cell, an immune cell (e.g., a T-cell, a B-cell, a macrophage, a neutrophil, a basophil, a mast cell, an eosinophil), etc. In some cases, the cell is a cancer cell. In some cases, the cell is a stem cell (e.g., an embryonic stem cell, an induced pluripotent stem cell, a mesenchymal stem cell, or the like) or is derived from a stem cell. The cell may be a primary cell or an immortalized cell. In some cases, the cell is a primary mammalian neuron (e.g., human cortical neuron, rat cortical neuron, etc.).

Thus, for instance, a variety of different cell types may be exposed to a common biological effector in certain embodiments, e.g., to determine the effect of the common biological effector on such cells. For example, the biological effector may be a small molecule, RNA, DNA, a peptide, a protein, or the like. As non-limiting examples, the cell types may be bacteria or other prokaryotes, and the common biological effector may be a suspected drug or antimicrobial agent. In some cases, at least 10, at least 20, at least 30, at least 40, at least 50, at least 60, at least 70, at least 80, at least 90, at least 100 cells, at least 500 cells, at least 1000 cells, at least 5000 cells, at least 10,000 cells, at least 50,000 cells, at least 100,000 cells, at least 150,000 cells, at least 200,000 cells, at least 250,000 cells, at least 300,000 cells, or at least 500,000 cells, etc. may be studied. For example, the different cell types may each be placed into distinct wells of a multiwell plate, and nanowires inserted into the cells placed in each of the wells to insert a common biological effector.

In another set of embodiments, different common biological effectors may be studied, e.g., as applied to a single or clonal population of cells, or to a variety of different cell types such as those discussed above. For instance, the wells of a multiwell plate may contain nanowires, and at least some of the nanowires may be at least partially coated with a variety of biological effectors. For example, at least 10, at least 20, at least 30, at least 40, at least 50, at least 60, at least 70, at least 80, at least 90, at least 100, at least 500, at least 1000, at least 5000, at least 10,000, at least 50,000, at least 100,000, at least 150,000, at least 200,000, at least 250,000, at least 300,000, or at least 500,000, etc. different biological effectors may be studied. In some cases, the biological effectors may be added to the wells and the nanowires using robotic systems such as those discussed herein. Accordingly, cells placed in the wells of the multiwell plate may encounter different biological effectors, as inserted by the nanowires. As a non-limiting example, the different biological effectors may represent a plurality of suspected candidate drugs, and the effects of the various candidate drugs on a given population of cells may be studied to identify or screen drugs of interest.

In addition, it should be noted that in some embodiments, the cells may be cultured on the substrate using any suitable cell culturing technique, e.g., before or after insertion of nanowires. For example, mammalian cells may be cultured at 37° C. under appropriate relative humidities in the presence of appropriate cell media. Thus, for instance, the effect of a candidate drug (or a plurality of candidate drugs) on the effect of a suitable population of cells may be studied.

In another aspect, cells may be electroporated using nanowires as discussed herein, e.g., to introduce molecule of interest into a cell, and/or to withdraw molecules from cells. In some cases, the nanowires may be used to create an electric field sufficient to cause electroporation to occur in at least some of the cells. Those of ordinary skill in the art will be familiar with cell electroporation techniques. For example, in some cases, an electric field may be applied such that the transmembrane potential exceeds a threshold level around 0.25 to 1 V, wherein the lipid bilayer of cell membranes may rearrange to form hydrophilic pores (typically between 20-120 nm in diameter). Any molecule smaller than the pore size can flow into the cell, e.g., by electrophoresis or diffusion. In some cases, the applied voltages may be at least about 1 V, at least about 2 V, at least about 3 V, at least about 4 V, at least about 5 V, at least about 10 V, at least about 15 V, at least about 20 V, at least about 25 V, or at least about 30 V, etc. In certain cases, for electroporating cells suspended in a solution, pulses of around 1000 V (varying with cell size) lasting a few microseconds to a millisecond may be used. In some cases, the applied voltages may be at least about 100 V, at least about 200 V, at least about 300 V, at least about 500 V, at least about 800 V, at least about 1000 V, at least about 1200 V, etc. The electrical field can be applied, e.g., as an electrical current or voltage signal. The waveform may be, e.g., a square, triangular, sawtooth, or sinusoidal shape, and may have any suitable duration, e.g., at least about 1 µs, at least about 5 µs, at least about 10 µs, at least about 50 µs, at least about 100 µs, at least about 500 µs, at least about 1 ms, at least about 3 ms, at least about 5 ms, at least about 10 ms, at least about 30 ms, at least about 50 ms, at least about 100 ms, at least about 500 ms, at least about 1 s, and/or no more than about 1 s, no more than about 500 ms, no more than about 100 ms, no more than about 50 ms, no more than about 30 ms, no more than about 10 ms, no more than about 5 ms, no more than about 3 ms, no more than about 1 ms, no more than about 500 µs, no more than about 100 µs, no more than about 50 µs, no more than about 10 µs, no more than about 5 µs, no more than about 1 µs, etc. Combinations of any of these are also possible, e.g., the duration may be between about 1 ms and about 3 ms or between about 1 µs and about 1 s.

In yet another aspect, cells, such as neurons, are positioned in electrical communication with one or more nanowires, e.g., as discussed herein. The nanowires may be used to stimulate the cells, and/or determine an electrical condition of the cells. More than one nanowire may be positioned in electrical communication with the cell, for example, in distinct regions of the cell. In some cases, the nanowires may be positioned such that they are relatively close together, for example, spaced apart by no more than about 200 nm. The nanoscale wires may be disposed on a substrate, and the cells may be adhered or plated onto the substrate, for example, using cell adhesion factors such as polylysine.

In one aspect of the invention, cells such as neurons are positioned in electrical communication with one or more nanowires, as described herein. Practically any cell can be used which exhibits electrical behavior, such as membrane potential. For instance, the cell may be a cell in which it is desired to measure the membrane potential (e.g., instantaneously, as a function of time, in response to an external stimulus, such as a drug or an applied external electrical potential, etc.), the cell may be a cell which can be used to detect electric fields (for example, cells from the ampullae of Lorenzini, which is present in certain types of organisms such as sharks), or the cell may be a cell that can produce an electrical signal, for example, a neuron (which is able to produce an action potential), a cardiomyocyte, or an electrocyte (which is used in organisms such as electric eels or electric ray to produce an electrical discharge). In some cases, a neuron comprises one or more ion channels (e.g., a voltage-gated ion channel, a ligand-gated ion channel). In certain cases, the ligand-gated ion channel of a neuron is a cholinergic receptor (e.g., a protein that responds to the binding of acetylcholine). The cholinergic receptor may, in some cases, belong to the family of neuronal nicotinic acetylcholine receptors (nAchRs). Neuronal nicotinic acetylcholine receptors, which are typically pentameric complexes comprising different combinations of alpha (e.g., $\alpha 2$-$\alpha 10$) and beta (e.g., $\beta 3$, $\beta 4$, $\beta 5$) subunits, may be a potential drug target for neurological disorders such as Parkinson's disease, Alzheimer's, and/or hyperactivity disorders.

The nanowire may be in electrical communication with a portion of the cell, i.e., the nanowire may be positioned, relative to the cell, such that the nanowire is able to determine or affect the electrical behavior of the cell, and/or of a region of the cell. The nanowires are typically of dimensions such that the nanowire can be used to measure or determine a distinct region of a cell. As a non-limiting example, if the cell is a neuron, the nanowire may be positioned such that the nanowire is able to determine or affect the electrical behavior of a portion of the axon, dendrite, and/or soma of the neuron. The nanowire may be in physical contact with the cell, or not in physical contact but positioned such that changes in the electrical state of the cell are able to affect the electrical state of the nanowire, and/or vice versa. In some embodiments, at least a portion of the nanowire is inserted in the cell. One or more than one nanowire may be in electrical communication with the cell.

In one set of embodiments, a cell in electrical communication with a nanowire can be electrically stimulated by passing a current or applying a potential to the nanowire, which may be used to affect the electrical state of the cell. For example, the membrane potential of a cell may be altered upon electrical stimulation, or a neuron can be stimulated to cause the neuron to polarize (e.g., hyperpolarize) or depolarize upon the application of sufficient current or potential. In some cases, a current or potential may be applied to the nanowire by a stimulator unit. Additionally, in some cases, the electrical state of the cell can be determined using a sensing electrode, such as another nanowire, as discussed below.

In another set of embodiments, a change in an electrical state of a cell, such as cell polarization or depolarization, an action potential, a change in plasma membrane potential (e.g., a postsynaptic potential), or the like may cause a change in the electrical state of a nanowire in electrical communication with the cell, such as a change in conductance, which change can be determined and/or recorded in some fashion, e.g., using techniques known to those of ordinary skill in the art. In some cases, the change in electrical state (e.g., an electrical signal) may be stored (e.g., in digital memory), output to a display, and/or modified/converted in some manner. Accordingly, one embodiment of the invention provides for the determination of an electrical state of a cell using a nanowire. According to some embodiments, at least a portion of the nanowire is inserted in the cell (e.g., in the intracellular space). In some cases, an electrical signal may be transmitted from the cell to the nanowire, and the signal may subsequently be transmitted to an amplifier unit in electrical communication with the nanowire. In some cases, the cell may also be one which was electrically stimulated, e.g., electrically stimulated by applying current or a potential to an electrode, such as another nanowire, that is in electrical communication with the cell. As a specific example, the electrical state of a neuron, or a portion thereof (e.g., an axon, a dendrite, a soma, etc.) may be determined using a nanoscale wire in electrical communication with the neuron; for instance, the neuron may depolarize (e.g., due to exposure to a chemical species, or to a nanoscale wire or other electrode able to cause the neuron to depolarize), causing the formation and propagation of an action potential through the neuron, which action potential may be determined using a nanowire. In this way, one or more than one neuron may be studied. In some embodiments, electrical signals from one or more neurons forming an interconnected network may be recorded using one or more nanowires. Accordingly, the characteristics of an interconnected network (e.g., a neuronal network) may be investigated.

In some embodiments, the electrical state of the cell may be altered by exposing the cell to a chemical species suspected of being able to alter the electrical state of the cell. For example, a chemical species able to facilitate the depolarization of a cell, or a chemical species that inhibit the depolarization of a cell, can be used to alter the electrical state of the cell, and in some cases, to cause a cell such as a neuron to polarize (e.g., hyperpolarize) or depolarize. In one set of embodiments, the chemical species comprises drugs or drug candidates, neurotoxins, neurotransmitters, or the like, which may be suspected of being able to treat or alter the behavior of the cells. In some cases, the drugs or drug candidates may target one or more types of ion channels. As a non-limiting example, the drugs or drug candidates may target neuronal nicotinic acetylcholine receptors (nAchRs).

Due to their small size, more than one nanowire may be positioned in electrical communication with the cell, or portion thereof, according to another set of embodiments. For example, at least 3, at least 4, at least 5, at least 10, at least 15, at least 20, at least 25, at least 30, at least 35, at least 40, at least 45, or at least 50 or more nanowires may be positioned in electrical communication with the cell, or with a portion thereof, e.g., axons and/or dendrites if the cell is neuron. In some embodiments, more than one nanowire may be inserted in the cell, or portion thereof. For example, at least 3, at least 4, at least 5, at least 10, at least 15, at least 20, at least 25, at least 30, at least 35, at least 40, at least 45, or at least 50 or more nanowires may be inserted in the cell, or with a portion thereof. Thus, a plurality of nanowires may each be used in some embodiments to independently measure a distinct region of the cell. If more than one nanoscale wire is present, the nanowires may each independently be the same or different.

In some cases, the nanowires may be positioned relatively close to each other. For instance, the nanowires may be positioned such that they are separated by a distance of no more than about 200 nm, about 150 nm, or about 100 nm. In some cases, the nanowires may be positioned such that they are substantially parallel to each other. In some cases, cells may be positioned such that it is in contact with at least some of the nanoscale wires.

In one set of embodiments, the nanoscale wires and/or the cells are positioned on the surface of a substrate. Suitable substrates and substrate materials are discussed in more detail herein. In some cases, the surface of the substrate may be treated in any fashion that allows binding of cells to occur thereto. For example, the surface may be ionized and/or coated with any of a wide variety of hydrophilic and/or cytophilic materials, for example, materials having exposed carboxylic acid, alcohol, and/or amino groups. In another set of embodiments, the surface of the substrate may be reacted in such a manner as to produce carboxylic acid, alcohol, and/or amino groups on the surface. In some cases, a cell adhesion factor may be used to facilitate adherence of the cells to the substrate, i.e., a biological material that promotes adhesion or binding of cells, for example, materials such as polylysine or other polyamino acids, fibronectin, laminin, vitronectin, albumin, collagen, or peptides or proteins containing RGD sequences. The cell adhesion factor may be deposited on all, or at least a portion of, the substrate.

Such devices may be used, for example, to determine the responses of neurons or other cells (e.g., healthy or diseased cells) to drug candidates or other substances, e.g., in a parallel fashion. In some cases, high-throughput screening of drug candidates may be performed using various embodiments as discussed herein, e.g., to screen for treatments for neurological disorders or other conditions. Examples of neurological disorders include, but are not limited to, Parkinson's, Alzheimer's, hyperactivity disorders, epilepsy, and autism. In some cases, certain embodiments may be used to screen drug candidates that may potentially target ion channels (e.g., voltage-gated ion channels, ligand-gated ion channels). In certain embodiments, the drug candidates may potentially target neuronal nicotinic acetylcholine receptors (nAchRs). According to some embodiments, the effects of drug candidates may be evaluated by studying the peak and steady-state components of measured currents as a function of drug concentration and/or treatment protocol.

In some cases, the device may interface with a neuronal network, e.g., to alter synaptic connection strengths or create artificial inter-neuron connections, or for repairing or engineering network dynamics (e.g., intracellular coupling enables single-cell resolution control, while parallelism enables global network control). In some cases, the device may form at least part of a neuroprosthesis. For example, by selectively stimulating a neuronal network, the device may augment sensory, motor, and/or cognitive abilities of a human and/or non-human animal. In some cases, certain devices may be used to combat neurological disorders, for example by suppressing seizures and/or providing brain circuit rebalancing.

Some aspects are directed to methods of fabricating devices comprising one or more nanowires and an integrated circuit. In some embodiments, the method is performed at relatively low temperatures. It may be advantageous, in certain cases, for the method to be performed at relatively low temperatures in order maintain the functionality of the integrated circuit. For example, in certain cases, an integrated circuit (e.g., a CMOS circuit) may lose functionality at relatively high temperatures (e.g., above 450° C.). Accordingly, in some embodiments, the methods are performed at temperatures of about 450° C. or less, about 400° C. or less, about 350° C. or less, about 300° C. or less, about 200° C. or less, or about 100° C. or less.

In certain embodiments, the method comprises depositing a protective layer on an integrated circuit (e.g., a CMOS chip). In some cases, the presence of a protective layer may advantageously inhibit chemical attacks on exposed portions of the CMOS chip during further processing steps, such as etching. The protective layer may also provide a high-quality underlying material for generation of nanowires. Suitable methods of deposition include, but are not limited to, physical vapor deposition (e.g., sputter deposition), chemical vapor deposition, atomic layer deposition, thermal evaporation, and/or electron beam evaporation. In some cases, the protective layer comprises an electrically conductive material. In certain embodiments, the electrically conductive material comprises a metal. Non-limiting examples of suitable metals include titanium (Ti), platinum (Pt), gold (Au), and aluminum (Al). The protective layer may have sufficient thickness to prevent diffusion of CMOS materials from the integrated circuit to the top of the protective layer during subsequent processing steps. The thickness of the protective layer may, in some cases, be at least about 100 nm, at least about 200 nm, at least about 500 nm, at least about 1 µm, at least about 1.5 µm, or at least about 2 µm. In some cases, the thickness of the protective layer is about 2 µm or less, about 1.5 µm or less, about 1 µm or less, about 500 nm or less, about 200 nm or less, or about 100 nm or less, etc. Combinations of the above-noted ranges are also possible (e.g., about 200 nm to about 2 µm). In some cases, the protective layer has a substantially uniform thickness. In some embodiments, the protective layer is substantially smooth.

In some embodiments, the method comprises depositing a nanowire-material-comprising layer on the integrated circuit or the protective layer. Non-limiting examples of suitable deposition methods include plasma-enhanced chemical vapor deposition (PECVD), sputtering, and/or atomic layer deposition (ALD). In certain embodiments, the nanowire-material-comprising layer comprises silicon dioxide ($SiO_2$). However, the nanowire-material-comprising layer may comprise any material suitable for the formation of nanowires. For example, the nanowire-material-comprising layer may comprise silicon, silicon nitride, silicon carbide, iron oxide, aluminum oxide, iridium oxide, tungsten, stainless steel, silver, platinum, and/or gold. The nanowire-material-comprising layer may, in some cases, have relatively strong adhesion to an underlying layer (e.g., protective layer). In certain embodiments, the nanowire-material-comprising layer has a substantially uniform thickness. The nanowire-material-comprising layer may, in some embodiments, have a thickness in the range of about 1 micrometer to about 5 micrometers or about 1 micrometer to about 10 micrometers.

In some embodiments, the method further comprises forming an etch mask on the nanowire-material-comprising layer. In some cases, the etch mask comprises a positive resist. The positive resist may refer to a material that becomes soluble to a resist developer after being exposed to a beam of photons or electrons. When a beam of photons is used, the technique is generally termed photolithography, and when a beam of electrons is used, the technique is generally referred to as electron beam lithography. Examples of positive resists used in photolithography include, but are not limited to, poly(methyl methacrylate) (PMMA) and SPR220, S1800 series, and ma-P1200 series photoresists. Other examples of photoresists include, but are not limited to, SU-8, S1805, LOR 3A, poly(methyl glutarimide), phenol formaldehyde resin (diazonaphthoquinone/novolac), diazonaphthoquinone (DNQ), Hoechst AZ 4620, Hoechst AZ 4562, Shipley 1400-17, Shipley 1400-27, Shipley 1400-37, or the like. Examples of positive resists used in electron beam lithography include, but are not limited to, PMMA, ZEP 520, APEX-E, EBR-9, and UVS.

In some embodiments, at least a portion of the positive resist may be exposed to light (visible, UV, etc.), electrons, ions, X-rays, etc. For example, at least a portion of the positive resist may be exposed to light within a stepper. In some cases, the exposed portions of the positive may be dissolved. An etch mask comprising a plurality of substantially circular discs of positive resist may then be formed, according to some embodiments.

In some embodiments, a negative resist is used instead of (or in addition to) a positive resist. The negative resist may be a material that becomes less soluble to a resist developer after being exposed to a beam of photons or electrons. Several non-limiting examples of negative resists used in photolithography include SU-8 series photoresists, KMPR 1000, and UVN30. Additional non-limiting examples of negative resists used in electron beam lithography include hydrogen silsesquioxane (HSQ) and NEB-31. It should be appreciated that any positive resist, negative resist, or resist developer known in the art may be used. Resist developers for photolithography include aqueous solutions with either an organic compound such as tetramethylammonium hydroxide or an inorganic salt such as potassium hydroxide, and they may also contain surfactants. Resist developers for electron beam lithography may include methyl isobutyl ketone and isopropyl alcohol.

In some cases, the portions of the nanowire-material-comprising layer no longer protected by the photoresist may subsequently be etched (e.g., to form nanopillars). Any etching technique known in the art may be used. In some embodiments, a dry etching technique (e.g., reactive ion etching) may be used. In some cases, the nanowire-material-comprising layer may be further etched to form nanowires. In some cases, a wet etching technique (e.g., using an acid, such as buffered hydrofluoric acid) may be used for further etching.

According to some embodiments, the method further comprises conformally coating one or more nanowires with an electrically conductive material. In some embodiments, the electrically conductive material is a metal. Non-limiting examples of suitable metals include gold (Au), platinum (Pt), titanium (Ti), aluminum (Al), copper (Cu), chromium (Cr), and/or silver (Ag). In some cases, the electrically conductive material is a non-metal. A non-limiting example of a suitable non-metal is iridium oxide. Suitable coating techniques include, but are not limited to, contact lithography, sputtered metallization, thermal evaporation, electron beam evaporation, and/or atomic layer deposition. In some cases, a contact lithography step may be followed by a sputtered metallization step.

In certain embodiments, the conformally-coated nanowires may be selectively passivated by coating the integrated circuit and/or nanowire sidewalls with a substantially electrically insulating material. For example, in some embodiments, one or more conformally-coated nanowires may be coated with silicon dioxide ($SiO_2$), alumina ($Al_2O_3$), and/or hafnium oxide ($HfO_2$). Non-limiting examples of suitable coating techniques include atomic layer deposition (ALD), PECVD, sputtering, thermal evaporation, and/or electron beam evaporation. In some cases, the passivation layer may be relatively thin. For example, in a particular example, the passivation layer may comprise 200 nm alumina and 20 nm silicon dioxide. In some cases, the passivation layer may be etched to expose the electrically conductive coating (e.g., at the tips of the nanowires). Any etching technique known in the art may be used. In some embodiments, a wet etching technique may be used.

Figure 3:
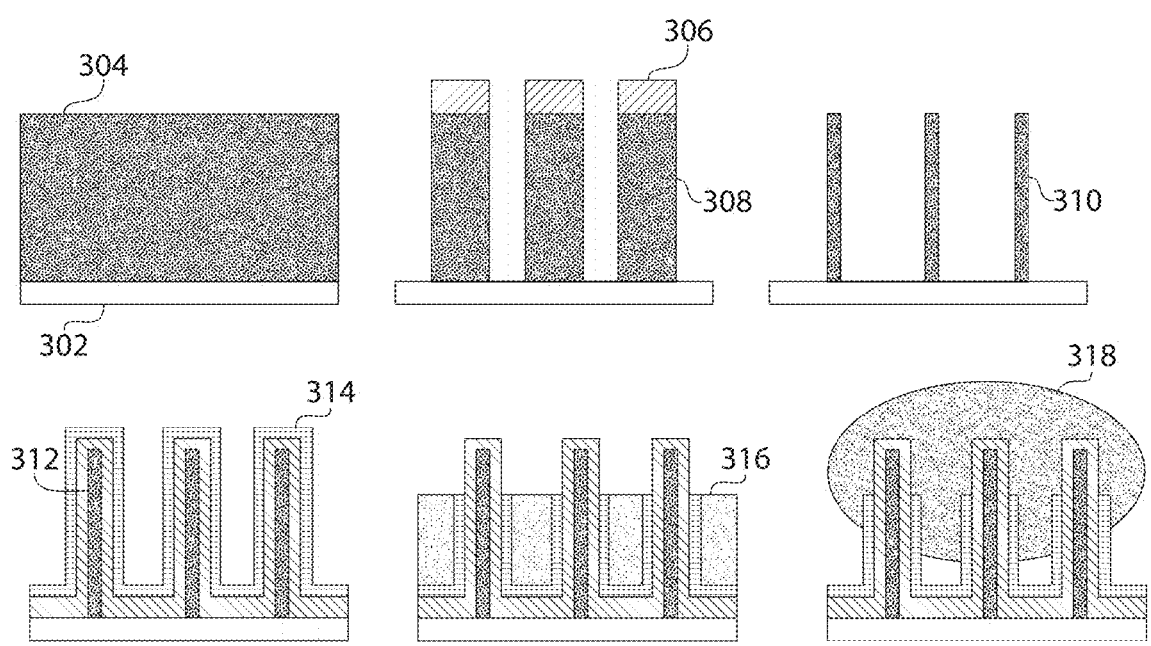
FIG. 3 is a schematic of a process for fabricating a device comprising nanowires and an integrated circuit, according to some embodiments.

An exemplary schematic illustration of a fabrication process is shown in FIG. 3. In FIG. 3, a protective layer 302 is coated on an integrated circuit (not shown) (e.g., via sputter deposition). A nanowire-material-comprising layer 304 is then deposited on protective layer 302 (e.g., via PECVD). A photoresist (e.g., positive resist) 306 is then coated on layer 304. Photoresist 306 is exposed to a source of light, and portions of photoresist 306 are dissolved, leaving circular discs of photoresist 306. The portions of layer 304 no longer protected by photoresist 306 are etched (e.g., via reactive ion etching), forming nanopillars 308. Nanopillars 308 are then be further etched (e.g., via an acid) to form nanowires 310. Nanowires 310 are subsequently conformally coated with an electrically conductive layer 312 and then further coated with a passivation layer 314. A portion of the coated nanowires are then further coated with a resist (e.g., spin coat resist), with the tips of the nanowires remaining uncoated. The tips of the nanowires are etched to remove passivation layer 314, exposing electrically conductive layer 312. The nanowires and integrated circuit are then ready for use with biological cell 318.

The following documents are incorporated herein by reference in their entireties: U.S. patent application Ser. No. 13/264,587, filed Oct. 14, 2011, entitled "Molecular Delivery with Nanowires," by Park, et al., published as U.S. Patent Application Publication No. 2012/0094382 on Apr. 19, 2012; International Patent Application No. PCT/US11/53640, filed Sep. 28, 2011, entitled "Nanowires for Electrophysiological Applications," by Park, et al., published as WO 2012/050876 on Apr. 19, 2012; International Patent Application No. PCT/US2011/53646, filed Sep. 28, 2011, entitled "Molecular Delivery with Nanowires," by Park, et al., published as WO 2012/050881 on Apr. 19, 2012; U.S. Provisional Patent Application Ser. No. 61/684,918, filed Aug. 20, 2012, entitled "Use of Nanowires for Delivering Biological Effectors into Immune Cells," by Park, et al.; and U.S. Provisional Patent Application Ser. No. 61/692,017, filed Aug. 22, 2012, entitled "Fabrication of Nanowire Arrays," by Park, et al. In addition, the following PCT applications, each filed on Mar. 15, 2013, are incorporated herein by reference in their entireties: International Patent Application No. PCT/US2013/032457, entitled "Use of Nanowires for Delivering Biological Effectors into Immune Cells"; International Patent Application No. PCT/US2013/032486, entitled "Fabrication of Nanowire Arrays"; and International Patent Application No. PCT/US2013/032486, entitled "Microwell Plates Containing Nanowires."

In addition, U.S. Provisional Patent Application Ser. No. 62/101,931, filed Jan. 9, 2015, entitled "Nanowire Arrays for Neurotechnology and Other Applications," by Park, et al.; and U.S. Provisional Patent Application Ser. No. 62/126,402, filed Feb. 27, 2015, entitled "Nanowire Arrays for Neurotechnology and Other Applications," by Park, et al., are each incorporated herein by reference in their entireties.

The following examples are intended to illustrate certain embodiments of the present invention, but do not exemplify the full scope of the invention.

EXAMPLE 1

One challenge of experimental neuroscience is to create tools that can perform intracellular and parallel recording/stimulation of electrophysiological activities in a mammalian neuronal network. Intracellular access is greatly desired due to its high sensitivity and clear cell-to-electrode registry (single-cell resolution). Parallel, simultaneous interrogation of a large number of neurons is necessary for studying the dynamics of a complex neuronal network as a whole. A tool enabling both of these tasks will have a translational impact in neuroscience and neurotechnology, yet no such tool is available. For example, the Nobel-prize winning patch clamp technique is a powerful method for intracellular recording and stimulation, but this glass pipette technique cannot be scaled for large-scale parallel measurements. The high-density microelectrode array, such as the Utah array, is suited for parallel recording, but the microelectrodes are too large to penetrate mammalian neurons, and thus they can perform only extracellular recording.

Figure 4A:
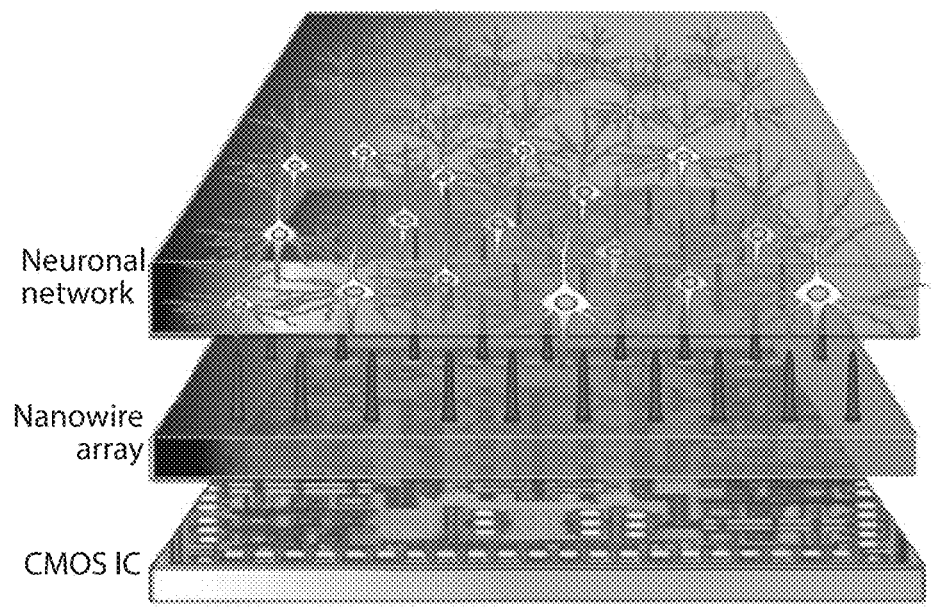
FIGS. 4A-4B illustrate certain devices in accordance with certain embodiments of the invention.
Figure 4B:
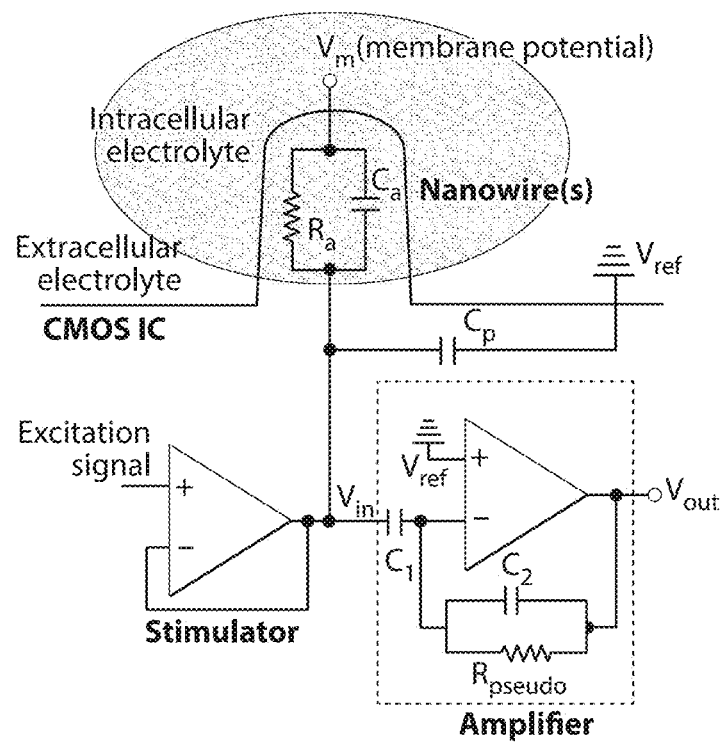

This example uses advances in CMOS technology to develop a practical forefront tool that can perform intracellular and parallel neuronal coupling at a large scale. For example, the number of nanowire recording sites may be about 10,000, and this nanowire array may be made "active" by fabricating it on top of a CMOS integrated circuit (IC) (FIG. 4A). Nanowires in each recording site are connected to their own amplifier and stimulator in the underlying IC (FIG. 4B) (i.e., the IC itself assumes an array structure with about 10,000 amplifiers and stimulators). The on-chip electronics in the IC may be used for one or more or roles, including the following. First, it makes practically possible the parallel operation of the large-scale nanowire site array. Second, the on-chip electronics proximate to the nanowires may increase the recording sensitivity, e.g., by avoiding a long signal path to off-chip electronics fraught with large stray capacitance that can attenuate a signal. This active—or CMOS-assisted—nanowire array may be applied for intracellular and massively parallel recording and stimulation of in vitro dissociated cultures of mammalian neuronal networks and ex vivo brain slices. This can also be used in the study of in vivo neuronal networks and the development of new types of neuroprosthetics.

The ability of this new device to perform intracellular and massively parallel neuronal interrogation facilitates drawing functional wiring diagrams of neuronal networks, offering a step toward understanding the machinery behind the brain. It also opens up new exciting vistas in neurotechnology. For example, the device can intracellularly examine the response of disease-affected neurons to drug candidates in a highly parallel fashion, enabling high-throughput pharmaceutical screening for neurological disorders. As another example, the device interfaced with a neuronal network can alter synaptic connection strengths or create artificial inter-neuron connections, repairing or engineering network dynamics (intracellular coupling enables single-cell resolution control, while parallelism enables global network control); therefore, the device may offer improved neuroprosthesis strategies to augment sensory, motor, and cognitive capabilities or to combat neurological disorders (e.g., suppression of seizures; brain circuit rebalancing in Parkinson's disease).

In one set of experiments, a CMOS IC was designed and fabricated with 32×32=1024 recording/stimulation sites (FIG. 5A); each site contained a metal pad on the top surface and an amplifier and a stimulator that connected to the pad. The feasibility of the post-fabrication of nanowires on the IC was demonstrated by defining 9 nanowires on each site's pad (FIG. 5B). To evaluate nanowire conductance in solution, the array was placed in extracellular solution, and a 1.5 V voltage step was applied to each site with respect to an Ag/AgCl reference electrode. Current was measured after 100 ms; the delay was designed to ensure that Faradic current was measured, as opposed to purely capacitive current through the insulating silicon dioxide on the nanowire sidewalls and pad. A dominant fraction (greater than 90%) of nanowires across the 1024-site arrays exhibited conductance in the expected range (e.g., above about 30 pA). Similar results were obtained for arrays comprising platinum-tipped nanowires and arrays comprising gold-tipped nanowires.

Figure 5A:
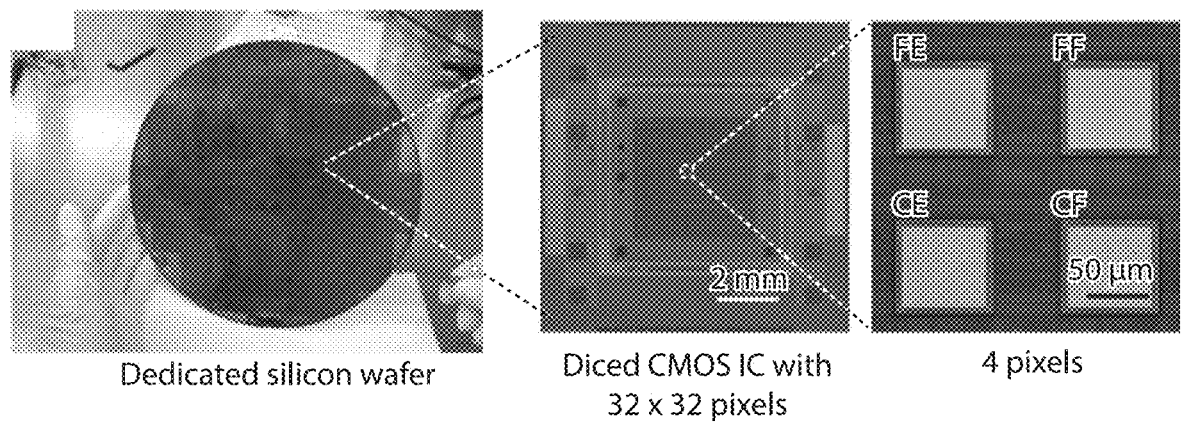
FIGS. 5A-5D illustrate a CMOS IC containing 1024 recording/stimulation sites, in accordance with one embodiment of the invention.
Figure 5B:
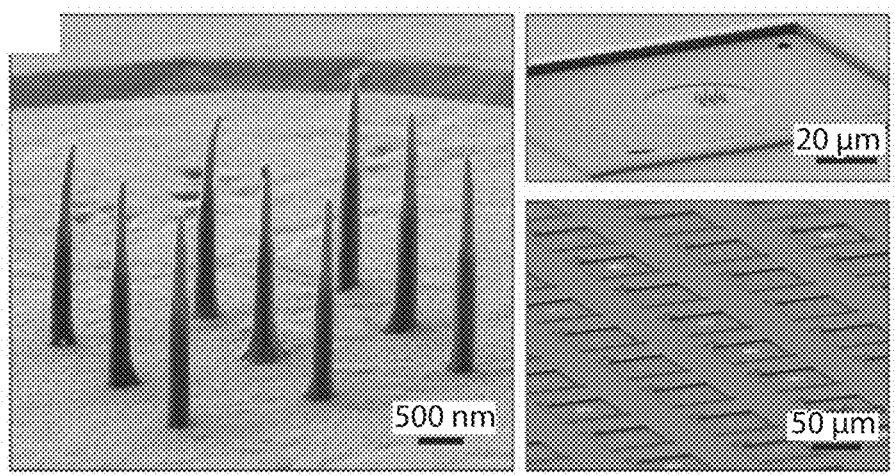
Figure 5C:
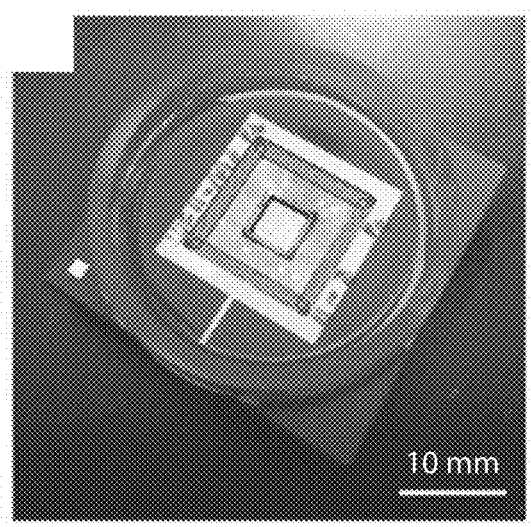
Figure 5D:
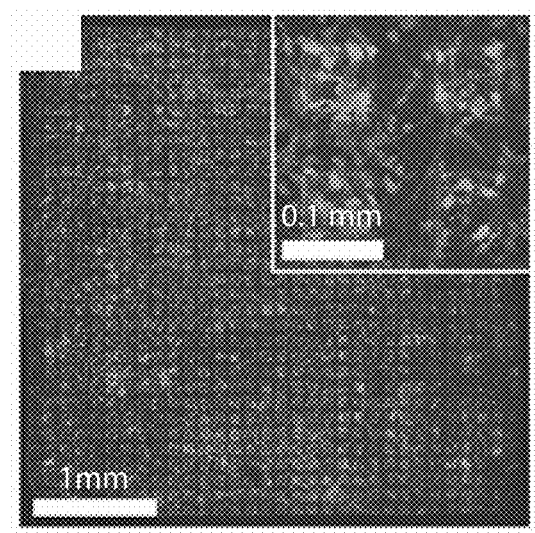

The packaged chip (FIG. 5C) was incubated with neuronal culture, used in salt solutions for electrochemical experiments, and re-used 4 times (FIG. 5D). This study also demonstrated the basic co-workings of the on-chip electronics and nanowires and the advantage of such combination: (1) by applying voltage pulses to nanowires via the site stimulator, neurons were induced to admit the nanowires (e.g., electroporation), with a high (greater than 70%) yield without affecting cell viability; (2) the site amplifier intracellularly recorded a time-varying membrane potential of a live neuron (FIG. 6) with the overall gain improved by 10 to 50 times from a prior passive nanowire array operated with off-chip electronics.

FIG. 5A shows a CMOS IC (middle) containing 32×32 sites. Each site contained an amplifier and a stimulator, both of which connected to the site's surface pad. FIG. 5B shows that on each site's pad, 9 vertical nanowires were fabricated. FIG. 5C shows the packaged device (IC and nanowires). FIG. 5D shows a fluorescent overlay of rat cortical neurons cultured across the array.

Figure 6:
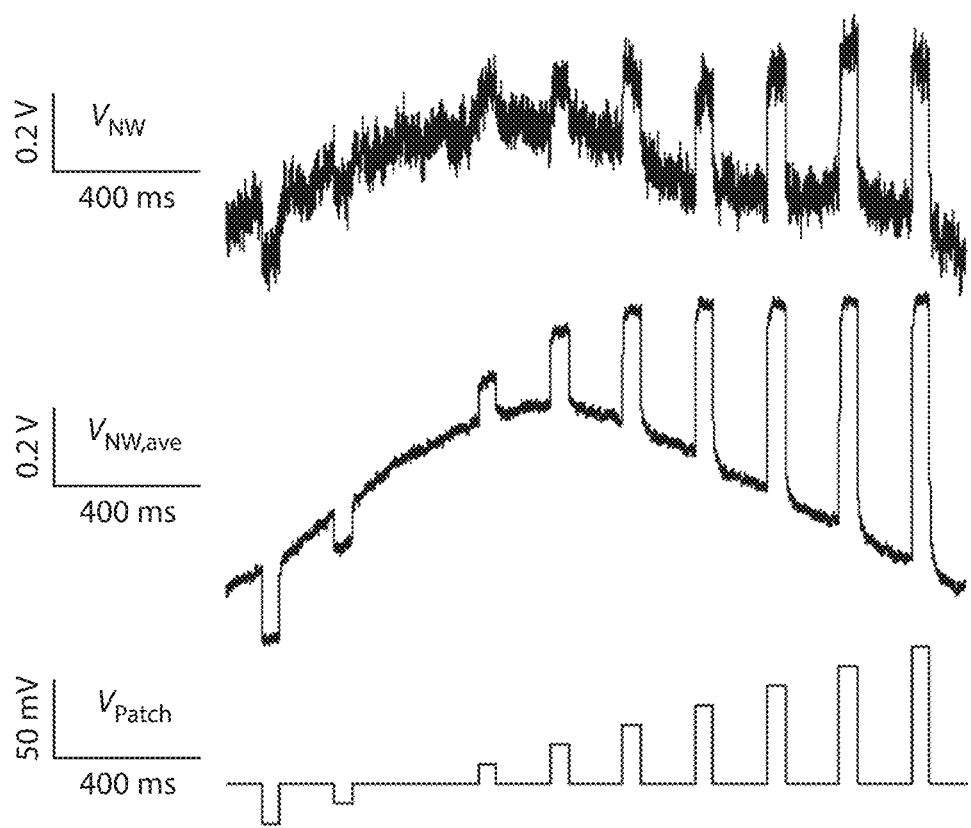
FIG. 6 illustrates voltage pulses applied to a rat cortical neuron, in another embodiment of the invention.

FIG. 6 shows that voltage pulses were applied to the cell membrane via a patch clamp to a rat cortical neuron (bottom). Through the nanowires, the site amplifiers recorded the resulting change in the membrane potential (top). Averaging 48 measurements cleaned up noise (middle). From the largest amplitude pulse of 70 mV, the membrane-to-nanowire attenuation was calculated to be about 25 V/V. Additional details about the experimental apparatus used in these experiments can be seen in Example 2, below. Because the site amplifiers recorded a pulse instead of a positive and negative spike, as would be expected from an extracellular measurement (which takes the derivative of a signal), these results demonstrated intracellular recording of an electrical signal from the neuron.

Large-scale intracellular neuronal recording and stimulation, the operation of the massively parallel array (say 128×128=16,384 sites) are also possible. For example, global digital control circuit in the IC may be implemented and used to sequentially yet rapidly scan the array from one sub-group to another. For example, in the recording mode, the 16,384 site amplifiers' outputs can be read by moving from one row (128 sites) to another row with a 2 MHz clock. Once all 128 rows are scanned after a time duration of 1/(2 MHz)×128~0.06 ms, the scan will repeat. The sampling rate for each site in this example is about 15 kHz, which is sufficient to resolve action potentials.

EXAMPLE 2

Figure 7:
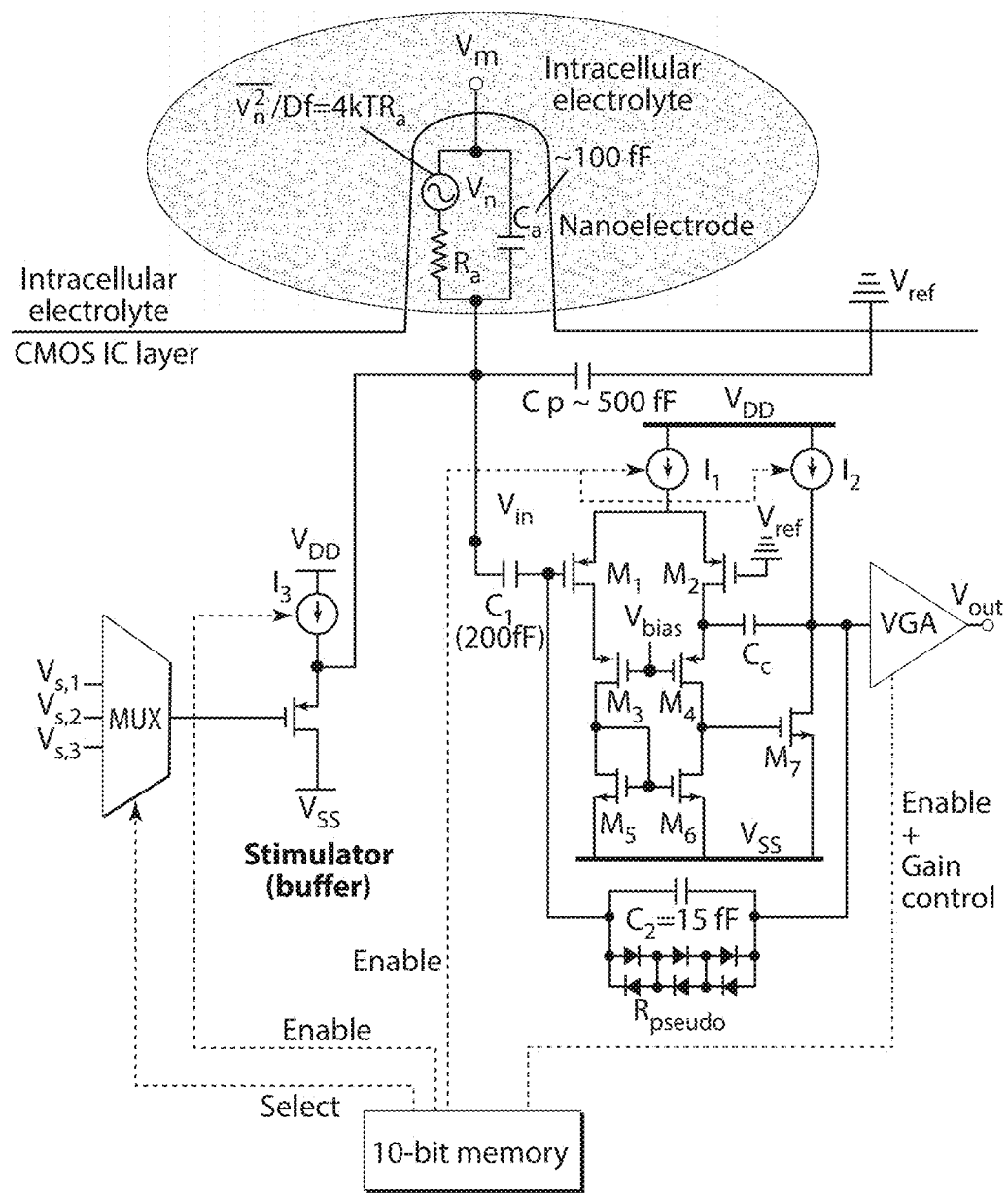
FIG. 7 illustrates a nanowire amplifier chain, in yet another embodiment of the invention.

This example illustrates one embodiment of the invention using CMOS. In this example, vertical nanowires are top-down defined on the CMOS chip, with the dimensions (150 nm diameter; 3 micrometers height), which are useful for coupling with biological cells. FIG. 7 is the nanowire-amplifier chain, the centerpiece of the array. The nanowire is modeled by the capacitor $C_a$ (about 100 fF) arising from the double layer formed between the electrode and intracellular electrolyte. The nanowire faradic resistance, $R_a$, is kept high (~T$\Omega$, teraohms) by AC coupling the front end of the amplifier, $C_1$, and therefore can be ignored. In this scheme, with no direct current, biological cells such as neurons are measured capacitively, which in turn maximizes the lifetime of the biological cells (not to be confused with the noninvasiveness of nanowire penetration). The capacitor $C_p$ (about 500 fF) models the parasitic coupling of the signal path with the extracellular electrolyte.

The biological signals of interest to be measured through the nanowire-amplifier chain include both post synaptic potentials (PSPs) and action potentials (APs). These signals have low amplitude ($V_m$ is about 3 mV for PSPs and about 100 mV for APs) and low frequency (about 1 Hz to about 100 Hz for PSPs and about 0.1 kHz to about 20 kHz for APs), which can readily lend themselves to contamination by 1/f noise. This is compounded by the large nanowire impedance due to $C_a$, which, in conjunction with $C_p$ and amplifier input impedance, divides down the signal voltages significantly.

The first stage amplifier, a single-ended low noise amplifier (LNA), is used for signal processing as it determines the signal-to-noise ratio (SNR) of the recorded signals. A simple two stage opamp topology, FIG. 7, is used to minimize the number of MOSFETs, namely noise sources, in play. Traditionally, high currents and large MOSFETs would be used to minimize noise. For compatibility with biological cells, however, low power is required to minimize heat dissipation (causing damage to cells) and minimal pixel area is required to be on the same dimension of the cell size (about 10 micrometers to 100 micrometers). The input pair, M1 and M2 in FIG. 7, also attenuates the signal due to its input capacitance being on the same order of the nanowire access capacitance, $C_a$, (about 100 fF). This design may be customized for specific nanowires used for biological cell interrogation.

A high-pass filter (a diode pseudo resistor in parallel with a poly-insulator-poly capacitor) is placed in the negative feedback path with a 5-Hz 1-pole cutoff. This filters in most information of PSPs, yet filters out dc drift and below-cutoff 1/f noise, both of which could otherwise saturate subsequent amplifiers. The use of diode pseudo resistor, FIG. 7, is used in this design. It provides a very high resistance (~TΩ, teraohms) within the pixel area constraint.

Figure 8:
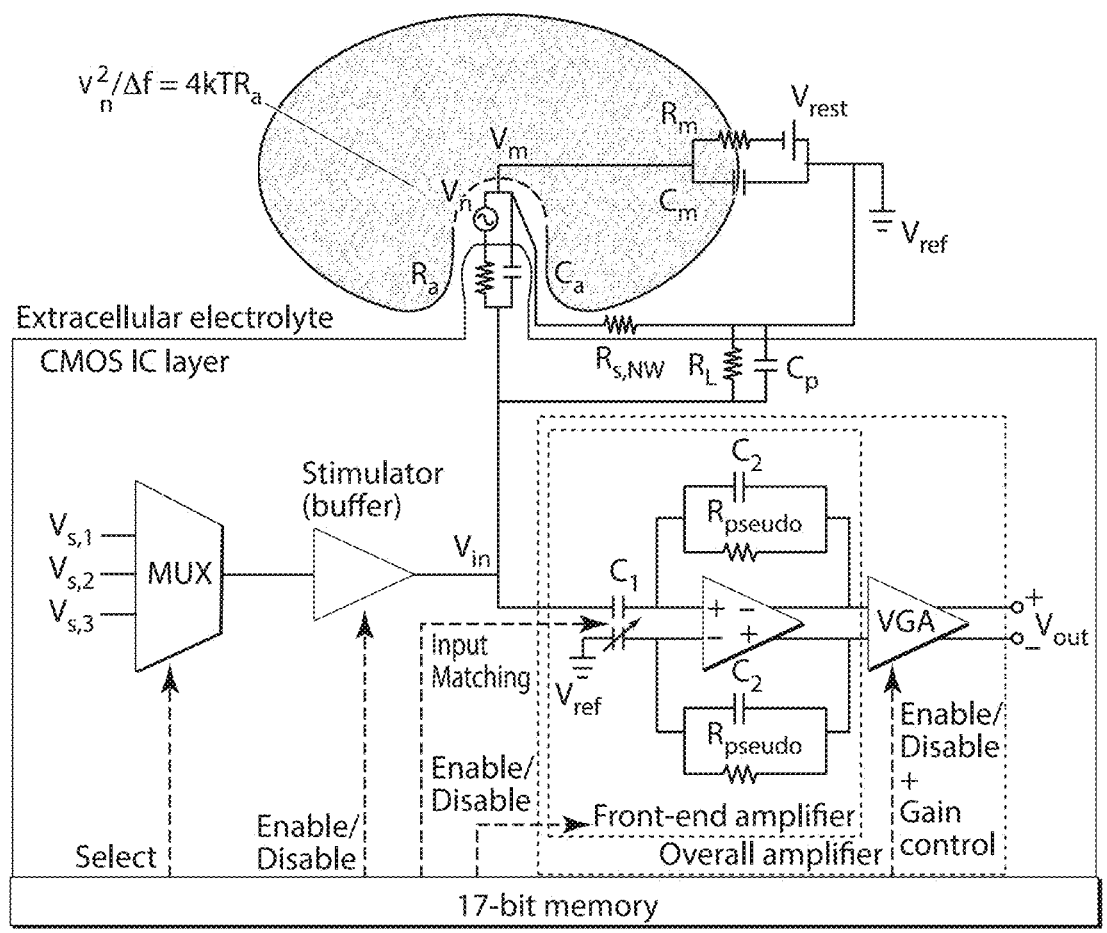
FIG. 8 illustrates a CMOS circuit, in another embodiment of the invention.

A variable gain amplifier (VGA) is used after the LNA in order to account for a wider signal range (PSP signals are about 1 mV and APs are about 100 mV) while maintaining good signal-to-noise ratio for routing off chip. The variable gain is controlled by a local digital memory (FIG. 7 and FIG. 8, bottom). The memory also allows the amplifier and stimulator (a buffer to apply one of three voltage stimulus sources to the nanowire) to be turned on and off, enabling very low power consumption, which is important to prevent damage to biological cells. The choice of voltage stimulus source (FIG. 7, left) is also controlled by the memory, allowing for different stimulation signals to be applied on different pixels, enabling biological network studies. In addition, the LNA and VGA amplifiers are also constructed in fully-differential form, FIG. 8, further reducing noise from common mode signals and increasing the output voltage range. An input variable capacitance array is included to match the capacitance of the nanowire, increasing the symmetry of the fully differential configuration and further reducing noise.

Figure 9:
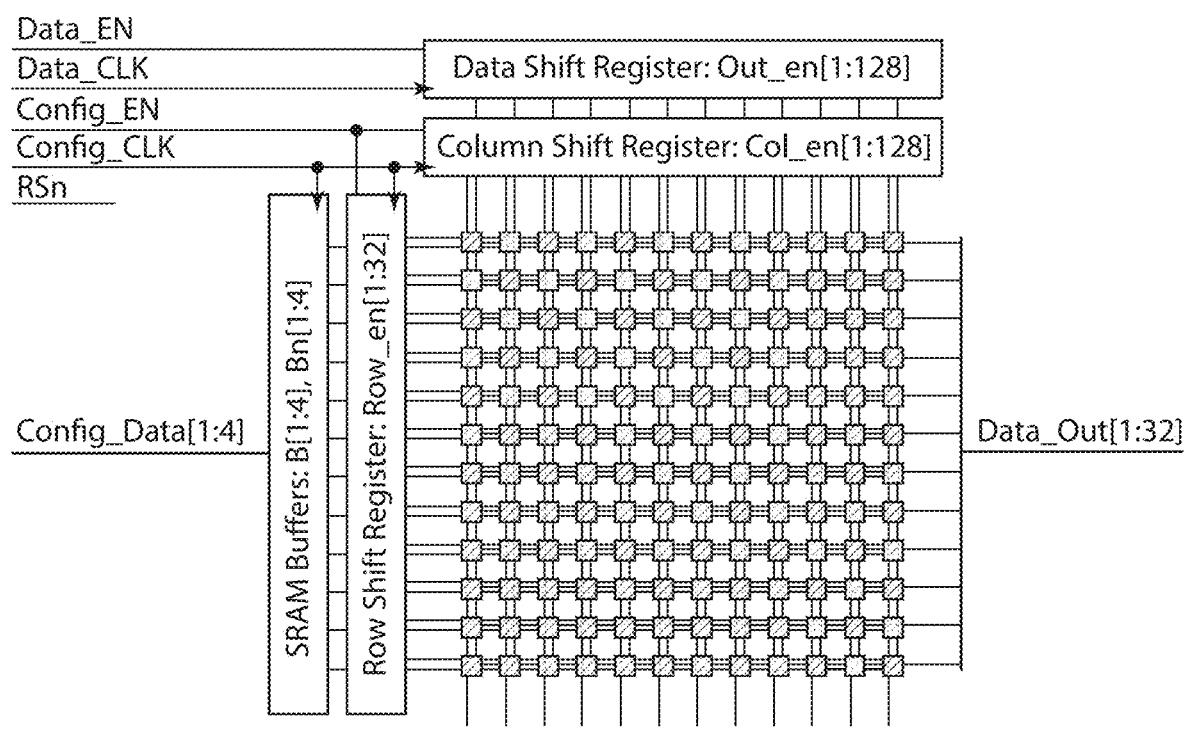
FIG. 9 illustrates an array in yet another embodiment of the invention.

An output multiplexer is used to allow for simultaneous recording of all pixels (FIG. 9). This allows for a large number of pixels while minimizing the number of output pins and maintaining a sample frequency, about 10 kHz, sufficient for resolving biological signals. The digital memory across the array, with four bits shown for representation in FIG. 9, allows individual programming of each pixel to stimulate, record, or be turned off. This minimizes power consumption through turning off pixels that are not used, while enabling network studies to be performed across a large number of pixels (pixels either stimulate or be read).

FIG. 7 shows a nanowire-amplifier chain. Substantial voltage division reduces $V_{in}$ from $V_m$. SNR may be optimized with this constraint. In addition to the noise produced by the amplifier, the nanoelectrode's resistance produces noise that is referred to the input of the amplifier. To accomplish a low frequency pole to reduce low frequency 1/f noise, a pseudo resistance composed of diodes is used in the feedback path allowing for greater than teraohm resistance or less than a 0.1 Hz pole. FIG. 8 shows a fully differential version of CMOS circuit. An input variable capacitance array is included to match the capacitance of the nanowire, increasing the symmetry of the fully differential. FIG. 9 shows a digital scheme for programming and reading from array. An output multiplexer is used to simultaneously record from all sites across the array while digital memory is used at each pixel for pixel configuration.

EXAMPLE 3

This example demonstrates intracellular recording of an electrical signal from a neuron using a nanowire in electrical communication with an integrated circuit, according to an embodiment of the invention. Embryonic rat hippocampus and cortical neurons were used.

Figure 10:
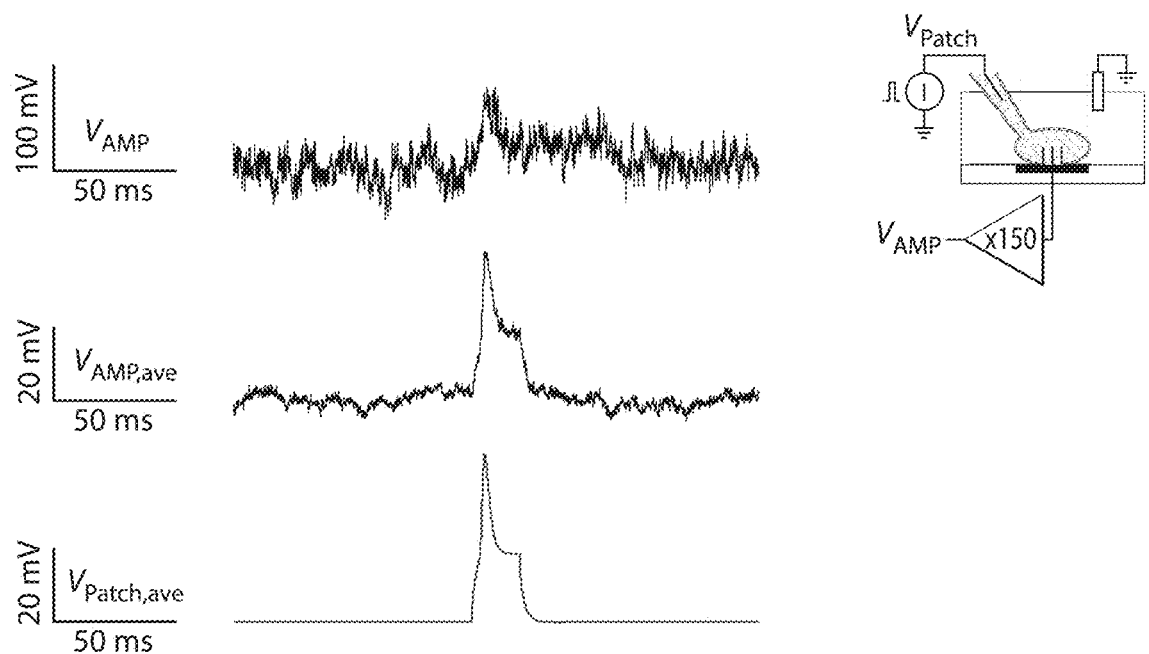
FIG. 10 illustrates voltage pulses recorded through a nanowire inserted in a neuron, according to an embodiment of the invention.

In this example, a patch clamp in current clamp mode was used to apply current pulses to a neuron. The applied current pulses caused the neuron to fire an action potential, which was read through the nanowire (which was inserted in the neuron) by an amplifier of the integrated circuit. The signal had an amplitude around 40 mV, and the membrane-to-nanowire attenuation was calculated to be about 100 V/V. Due to the close correlation between the output of the nanowire-connected amplifier (FIG. 10, top), the averaged output of the nanowire-connected amplifier (FIG. 10, middle), and the patch clamp (FIG. 10, bottom), these results demonstrated the capability of the nanowire-connected amplifier to intracellularly measure an electrical signal from a neuron.

EXAMPLE 4

This example demonstrates intracellular stimulation of a neuron using a nanowire in electrical communication with an integrated circuit, according to an embodiment of the invention. Embryonic rat hippocampus and cortical neurons were used.

Figure 11:
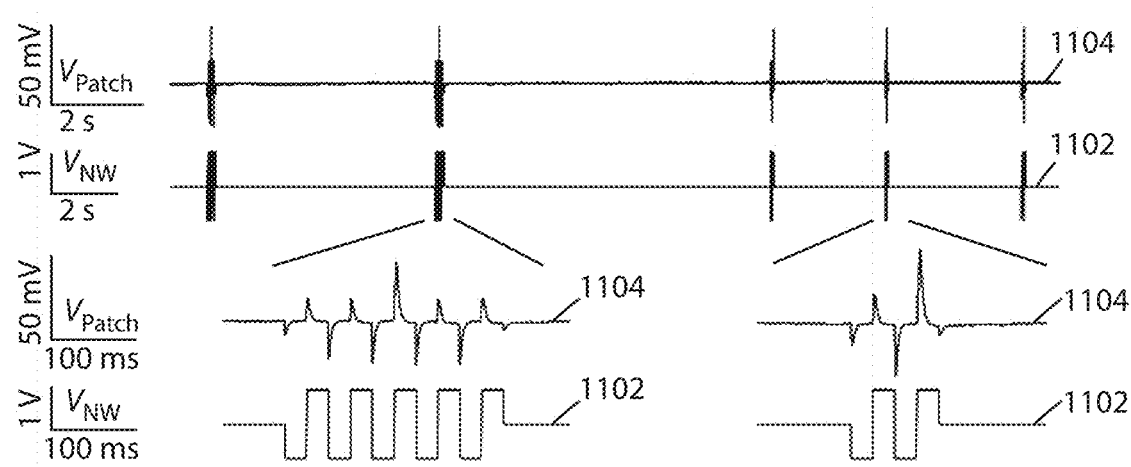
FIG. 11 illustrates voltage pulses applied to a nanowire inserted in a neuron, according to an embodiment of the invention.

In this example, biphasic voltage pulses were applied to the nanowire, which was inserted in the neuron. The response of the neuron was recorded by a patch clamp in current clamp mode. FIG. 11 shows the voltage pulses applied to the nanowire (1102) and the resultant electrical signals from the neuron (1104).

Five biphasic voltage pulses were applied to the neuron (FIG. 11, left). On the third pulse, there was a larger membrane response due to the neuron firing an action potential. Two biphasic voltage pulses were also applied to the neuron (FIG. 11, right). From FIG. 11, it can be observed that the neuron fired an action potential on the second pulse. Accordingly, this example demonstrates the ability of a nanowire in electrical communication with an integrated circuit to intracellularly stimulate a neuron.

EXAMPLE 5

This example demonstrates intracellular recording of electrical signals from a cardiomyocyte using a nanowire in electrical communication with an integrated circuit, according to an embodiment of the invention. A neonatal rat ventricular cardiomyocyte was used.

In this example, a nanowire was inserted into a cardiomyocyte, and electrical signals from the cardiomyocyte were recorded through the nanowire by an amplifier of the integrated circuit. Cardiomyocytes typically fire action potentials spontaneously, resulting in beating that can be observed with an optical microscope. Accordingly, a patch clamp is not needed for verification.

Figure 12:
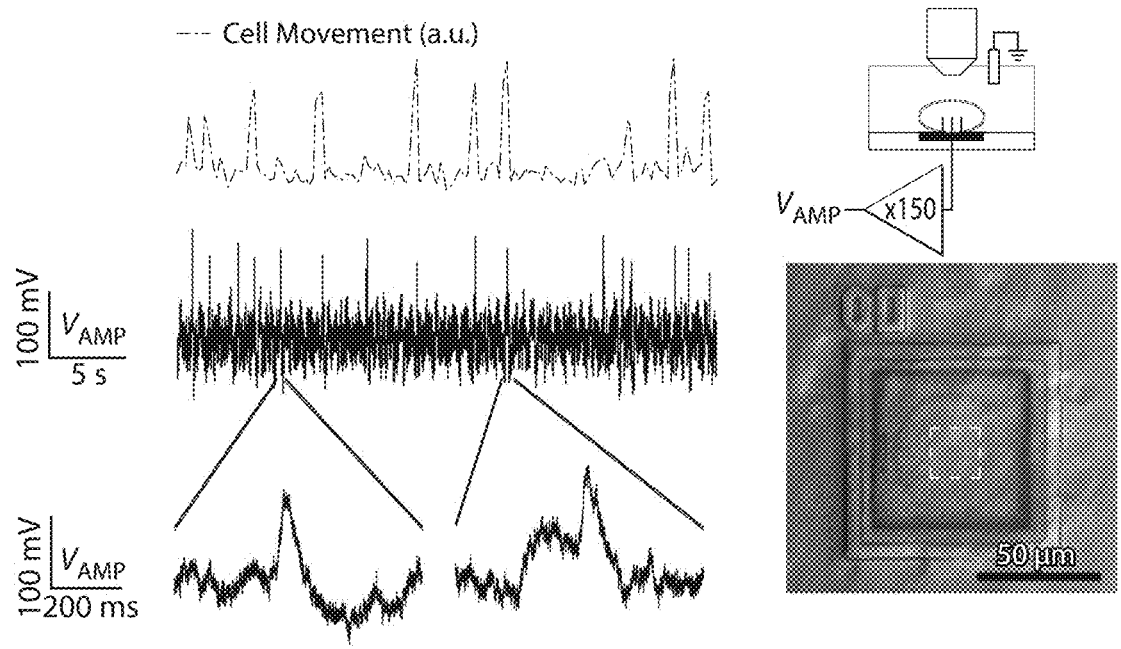
FIG. 12 illustrates, according to an embodiment of the invention, voltage pulses recorded through a nanowire inserted in a cardiomyocyte.

FIG. 12 shows cell movement (top), with peaks correlated to the beat of the cell. The cell movement was calculated from acquired images (e.g., the derivative of image acquisition). Electrical signals from the cardiomyocyte were recorded through the nanowire by the amplifier. The amplifier output is shown in the middle row of FIG. 12, with additional detail shown in the bottom row. From FIG. 12, it can be seen that action potential spikes recorded by the nanowire-connected amplifier (middle) were aligned with the beating of the cell movement (top). Some of the spikes recorded by the amplifier were not observed in the cell movement, but this may be accounted for by the low frame rate of image acquisition. The bottom row of FIG. 12 shows detail of a recorded action potential with good signal-to-noise ratio (left) and a recorded action potential that shows sub-threshold behavior, with the membrane rising before it fired an action potential (right).

This example thus demonstrated the ability of nanowire in electrical communication with an integrated circuit to record electrical signals from cardiomyocytes.

EXAMPLE 6

This example demonstrates intracellular stimulation of a cardiomyocyte using a nanowire in electrical communication with an integrated circuit, according to an embodiment of the invention. A neonatal rat ventricular cardiomyocyte was used.

Figure 13:
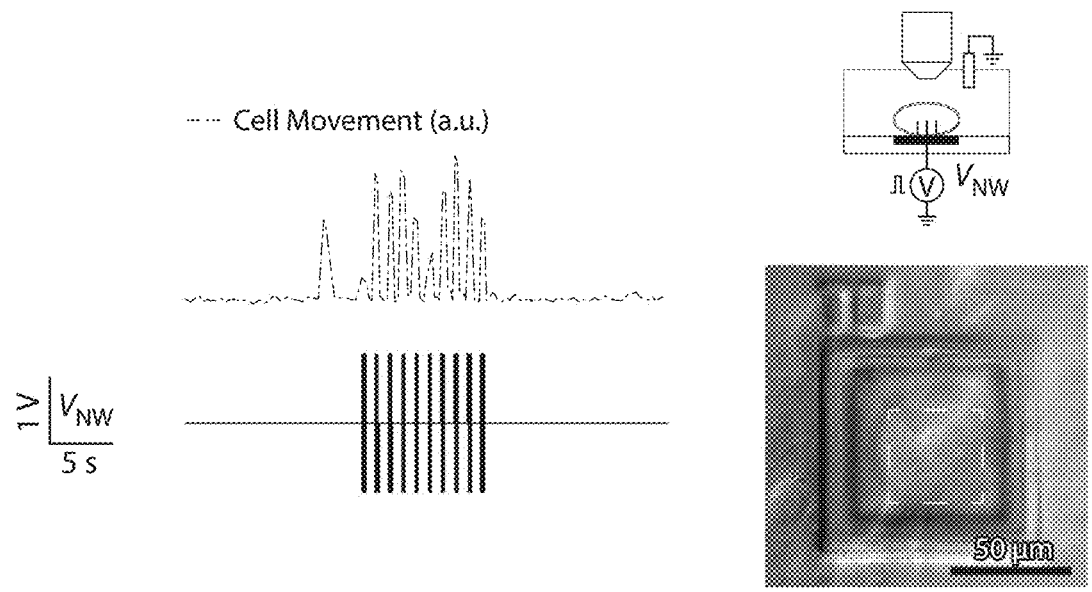
FIG. 13 illustrates, according to an embodiment of the invention, voltage pulses applied to a nanowire inserted in a cardiomyocyte.

FIG. 13 shows cell movement (top), with peaks correlated to the beat of the cell. Initially, the cardiomyocyte was beating at a relatively low frequency (e.g., about once every 30 seconds). Ten pulses were then applied at a frequency of about one pulse per second (bottom) to the nanowire, which was inserted in the cardiomyocyte. Upon application of the pulses, the cardiomyocyte fired an action potentials at a frequency corresponding to the applied pulses. This therefore demonstrated the ability of the nanowire to intracellularly stimulate a cardiomyocyte.

EXAMPLE 7

This example describes the use of an embodiment of the invention for therapeutic purposes.

In this example, vertical silicon nanowire (NW) electrodes are combined with backside complementary metal-oxide-semiconductor (CMOS) circuitry to form a high-throughput, scalable platform that can monitor and control the activity of neurons in complex networks of dissociated cultures and tissue preparations. This CMOS nanowire electrode array (CNEA), which comprises about 250,000 recording/stimulation sites, is well-suited for high-throughput electrophysiological screening, the most direct method of measuring neuronal activity.

The CNEA platform enables intracellular recording and stimulation of neuronal activity in primary mammalian neurons in a similar fashion to patch clamp pipettes. Moreover, it facilitates high-throughput, massively parallel measurements of individual neurons as well as of interconnected neurons in a network, measurements that are currently only possible at the scale of a few cells. These capabilities make the CNEA platform an optimal assay for screening novel ion channel drug candidates in addition to helping elucidate the electrophysiological characteristics cellular mechanism of the corresponding neurological disorders.

Neuronal activity is largely mediated by ion channels, which are membrane-spanning proteins that gate the flow of specific small ions in and out of cells in response to chemical or electrical stimuli. Defects in ion channels are the basis of a wide variety of neurological disorders. Neuronal nicotinic acetylcholine receptors (nAchRs) are cholinergic receptors that represent a superfamily of ligand-gated ion channels. NAchRs are generally pentameric complexes comprising different combinations of alpha (α2-α10) and beta β3, β4, β5) subunits. Some subtypes are widely distributed throughout the central nervous system while others are found only in rather restricted areas. These receptors are emerging as potential drug targets for a variety of neurological diseases including Parkinson's disease (PD), Morbus Alzheimer, and hyperactivity disorders. These neuronal pathologies are classified as multifactorial disorders caused by a combination of genetic susceptibility and environmental factors. PD—a movement disorder characterized by tremor, rigidity, and bradykinesia—is one of the most common progressive neurodegenerative disorders in the United States. Variants in nAchR genes have been identified as highly probable candidates associated with PD genetic risk factors. Despite the increased interest in their potential as druggable targets they remain underutilized, and their physiology as well as involvement in neuronal pathologies remains poorly understood.

Several nAchR subtypes expressed in the signaling pathway affected in Parkinson's disease have been identified, including the α4β2*, α6β2*, α4β2β3, and α4α6β2β3 subtypes. The α4α6β2β3 subtype is significantly affected even in moderate degeneration, making it a particularly relevant target for PD therapeutics. However, because of the complexity of the signaling pathway, a lack of optimal tools to study it, and a lack of highly selective receptor ligands, their exact role in PD is not fully understood. It remains unclear whether nAchR ligands exert their beneficial effects via receptor activation or blockage, leaving unresolved the question whether agonist or antagonist ligands would prove most beneficial for the treatment of PD symptoms.

The CNEA provides an ideal platform to elucidate their function and screen a multitude of potential therapeutic compounds in a high-throughput fashion in primary mammalian neurons, which cannot be studied with currently available high-throughput techniques. The CNEA can be used to comprehensively identify and classify the nAchR subtypes affected in PD and their corresponding phenotype using, for example, neurons extracted from validated Parkinsonian mouse models that recapitulate the symptoms and pathological features of PD. The CNEA can also be used to identify therapeutic compounds (e.g., compounds targeted at α4β2* and α6β2*) by screening and profiling the effects of the compounds on nAchR-subtype mediated currents. In particular, to characterize the modulatory effects of drug candidates, the modulation of the peak and steady state component of these currents as a function of drug concentration and treatment protocol can be measured and evaluated.

Another major line of research in drug discovery efforts for PD is focused on targeting pre- and postsynaptic sites in dopaminergic neurons. The rationale for such work stems from recent research suggesting that impairment in synaptic plasticity (activity-dependent changes in synaptic efficacy such as long-term potentiation (LTP) and long-term depression (LTD)) can result in the onset and progression of PD19. Electrophysiological measurements via whole-cell patch clamping in slices generated from PD mouse models have begun to elucidate the pre- and postsynaptic properties of direct-pathway and indirect-pathway synapses on medium spiny neurons. These pathways have been identified to contribute directly to the pathophysiologies of PD. In addition, efforts have been made to identify neuromodulators that can rescue normal synaptic modulation in PD mouse models aiming to identify potential targets for therapeutic treatment. However, these efforts have been limited by the low throughput of whole-cell patch clamp experiments. The CNEA, being able to simultaneously stimulate and record the activity of multiple connected neurons in dissociated cultures and tissue slice preparations, provides a well-suited platform to study and characterize these synaptic pathways at a much higher throughput, thus expediting the process of discovery of more potential drug targets as well as that of screening the effect of novel therapeutic compounds. The change in synaptic efficacy can be characterized by studying the change in amplitude as well as in the rising slope of evoked postsynaptic potentials (PSPs). The CNEA can be utilized to evoke and monitor PSPs in a spatially and temporally well-controlled manner. Studies in Parkinsonian mouse models have demonstrated that alterations in the subunit composition of N-methyl-D-aspartate (NMDA) receptors result in the impairment of synaptic plasticity, which in turn contributes to the pathological characteristics of PD. The CNEA can be used to screen therapeutic compounds targeting NMDA receptors with the goal of identifying compounds that can rescue normal LTP and/or LTD in PD models. Previous studies have demonstrated that endocannabinoids mediate LTD rescue in a PD mouse model, inspiring efforts towards the development of therapeutic compounds that modulate the levels of endocannabinoids being produced.

In addition to using the CNEA with mouse neurons, the CNEA can be used with human neurons derived from induced pluripotent stem cells (iPSCs) or directly induced from fibroblasts obtained from PD patients in order to validate and further characterize the most promising compounds in human-derived cells. Recently, iPSCs derived from PD patients have been successfully used to generate a broad variety of neuronal cell types and isolate the ones that are specifically involved in PD. These human-derived neurons offer an ideal system to screen novel therapeutic compounds in addition to validating findings of experiments with mouse models. Moreover, they enable the study and characterization of patient-specific disease phenotype and allow the development of personalized treatments. Accordingly, the CNEA platform enables high-throughput electrophysiological experiments with human-derived neurons in addition to allowing full integration with a variety of cellular assays, making possible truly multiplexed experiments.

EXAMPLE 8

Figure 14:
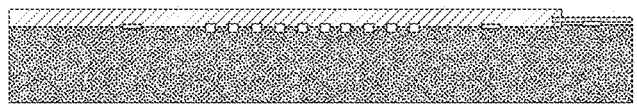
FIG. 14 is a schematic of a process for fabricating a device comprising nanowires and CMOS chips, according to an embodiment of the invention.
Figure 14:
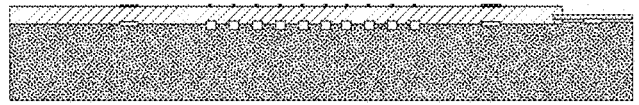
Figure 14:
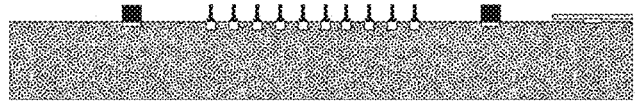

This example describes the fabrication of an integrated nanowire-CMOS device. The generation of the front nanoelectrode cellular interface array was achieved via a multi-level and complex nanofabrication process. The complexity of the nanofabrication process was due to the complementary metal-oxide-semiconductor (CMOS) technology, which typically can withstand full functionality if exposed only to temperatures below 450° C. In addition, the functional goals of the final device layout—a cellular interface that was intracellular, individual, and parallel—further extended the nanofabrication requirements and limitations. The fabrication process, summarized in FIG. 14, made possible the achievement of the ultimate functional aims while preventing any physical or functional damage to the underlying CMOS chip.

Initially, to prevent any functional or physical damage to the CMOS chip, the fabrication process began by protecting the CMOS exposed Aluminum-metal-layer-4 (Al-4) via sputter deposition of a Titanium (Ti) and Platinum (Pt) metal layer. The optimally thick and high-resolution Ti—Pt protection layer ensured: (1) inhibition of any chemical attacks of the exposed Al-4 possible during etch processing, (2) prevention of the Al-4 diffusion to the top of the protection layer during high temperature processes, and (3) generation of a high-quality underlying material for the generation of the top nanowire electrodes.

Second, to facilitate the generation of high-quality structural material for the nanowire electrodes and prevent any impairment of the CMOS chip, a plasma-enhanced chemical vapor deposition (PECVD) was developed to deposit silicon dioxide ($SiO_2$) at a temperature of only 350° C. The developed PECVD process included: (1) ensuring a highly clean substrate, (2) stabilizing the chamber vacuum, (3) ensuring a plasma chamber uniformity, (4) establishing a stable plasma prior to the deposition start, and (5) maintaining a low silane to nitrous ratio. To fabricate the vertical nanowire electrode array for interfacing two-dimensional in vitro cultures, a 3.5 µm-thick layer of $SiO_2$ was deposited via this PECVD process, which gave rise to an excellent uniformity and structural quality material with strong adhesion to the underlying pixel metal.

Subsequently, a stepper lithography process was developed to allow the generation of an accurately aligned, widely uniform (across the large pixel array), and high quality etch mask. The stepper lithography process was used to generate the array of the etch mask consisting of photoresist discs 1 µm in diameter—aligned centrally on top of the active pixel array. Such an etch mask facilitated the generation of the highly uniform array of vertical nanoelectrodes via reactive ion etching (RIE) of the surrounding $SiO_2$ surface. Once the characteristics of the RIE process were characterized and subsequently improved, a highly selective and reproducible $SiO_2$ etching was achieved that facilitated the generation of initial vertical structures with high aspect ratio and the designed vertical etch profile. Subsequently, $SiO_2$ isotropic wet etching was used to achieve the final structural profile of the vertical nanowire (length, 3 µm; diameter, 100 nm).

Next, electrical activation of the tips of the vertical nanowire electrodes in addition to conductive connection with the underlying metallized pixel was achieved through selective and conformal metallization. Contact lithography followed by sputtered metallization allowed the generation of a small grain metal layer with high conductivity and small grain size. The chip surface and nanowire sidewalls were then selectively passivated with 200-nm $Al_2O_3$ and 20-nm $SiO_2$, respectively, so that only the upper portion of each metalized nanowire was exposed. The final results of the fabrication process are summarized in FIG. 14.

The design, development, and optimization of the nanofabrication process flow facilitated the generation of an efficient interface between biological neuronal networks and the underlying electronic circuitry. First, the final profile geometry of the vertical nanowires made possible the intracellular interface of individual neurons. Secondly, the electrical properties of these nanoelectrodes (e.g., electrically conductive nanowire tips, selectively insulated base) provided direct electrical access to the cell's interior with minimal effect on cellular viability. Thirdly, the fabrication of the uniform nanoelectrode array (geometrically and electrically) across the CNEA chip allowed the generation of 1,024 independently addressable recording/stimulation sites at a 84-μm pitch in a 25-mm² area.

EXAMPLE 9

Intracellular recording is important in electrophysiology because it allows high fidelity study of ion channel activities in electrogenic cells. Concurrent recording of a large number of cells is desired for examining network dynamics and function. This example illustrates a solid-state electronic chip as a new concept electrophysiology tool that can address the long-standing intracellular vs. parallel dichotomy. The chip construct in this example is an array of vertical metallic nanowire electrodes (NWE) on the surface of a custom-designed CMOS integrated circuit (IC). The small electrodes can penetrate the cellular membrane, attaining intracellular access. Their top-down implementation into the large-scale array (1,024 sites) offers parallelism. It is the in situ electronic functions—amplification, stimulation, and multiplexing—of the underlying CMOS IC that may make possible the parallel operation of the intracellular nano-bio interface array.

This example demonstrates the parallel and intracellular recording/stimulation ability of this particular device with in vitro neonatal rat ventricular myocytes (NRVM) cultured on the chip. Network level analysis including action potential propagation is performed in this example using intracellular recordings from 364 NRVMs in the same tissue. Moreover, intracellular recording allows for investigation of important fine details of membrane potentials—such as early afterdepolarizations (EADs) caused by a $Na^+$ channel toxin, ATX-II—whereas parallel recording maps corresponding spatial propagations. The high-fidelity intracellular interrogation of large-scale electrogenic networks demonstrated in the present example can benefit not only pharmacological screening of ion channel drugs (used here as a demonstrational example) for cardiac and neuronal diseases, but also other applied and fundamental studies in electrophysiology.

Figure 15A:
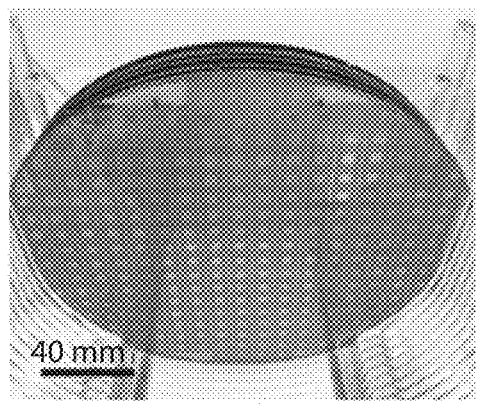
FIGS. 15A-15F illustrate arrays of nanowires with an IC, in some embodiments of the invention.
Figure 15B:
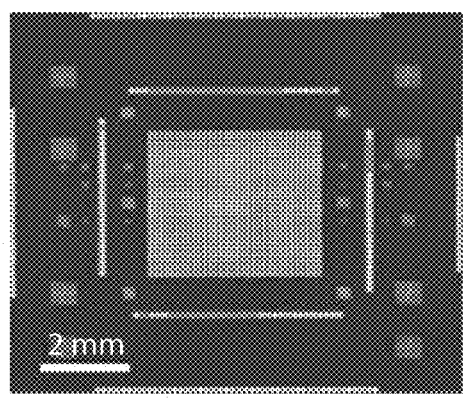
Figure 15C:
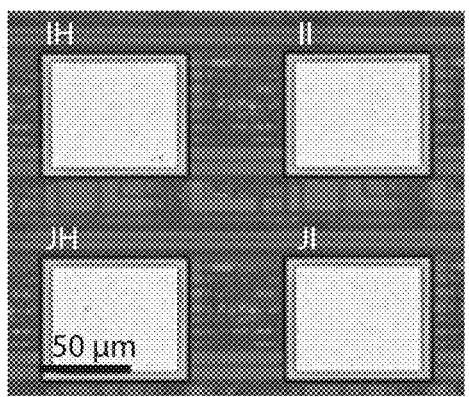
Figure 15D:
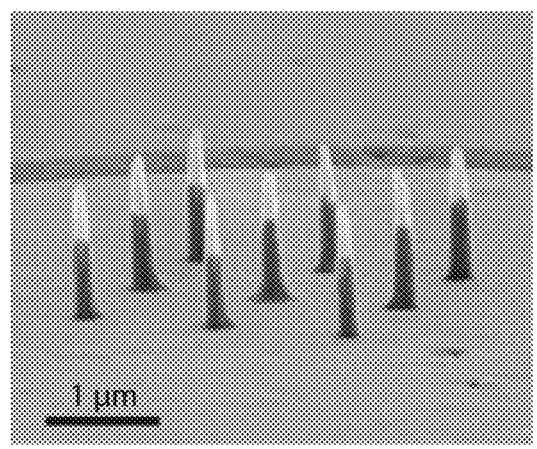

The ICs were custom designed IC in 5.0 V 0.35 micrometer CMOS technology (as shown in FIG. 15A and FIG. 15B). Each IC contained an array of 32×32=1024 recording/stimulation pixels where each pixel comprised of an amplifier, a stimulator, and a digital memory. The amplifier to record electrophysiological events and the stimulator to excite a cell were both connected to a metallic pad right above on the IC surface (see FIG. 15C). Nine vertical nanoelectrodes were then post-fabricated at the center of each pad (see FIG. 15D); each nanowire had a $SiO_2$ mechanical core, a thin Ti/Pt coating and $SiO_2$ insulation at the base. The exposed metal tip provided electrical access to intracellular matrix while the base $SiO_2$ passivation helped to form tight seals to the cell membrane. The 9 electrodes at each pixel were electrically connected together with the IC pad to increase the overall conductance and improve the electrophysiological signal amplitude.

Figure 15E:
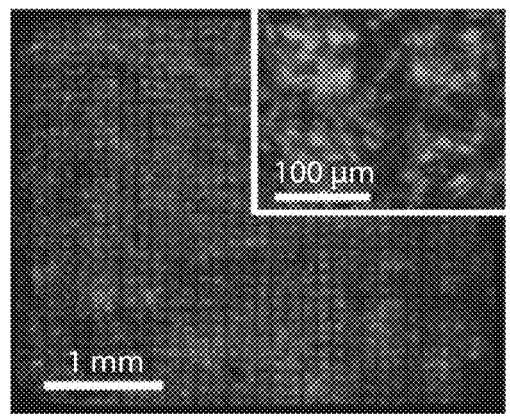
Figure 15F:
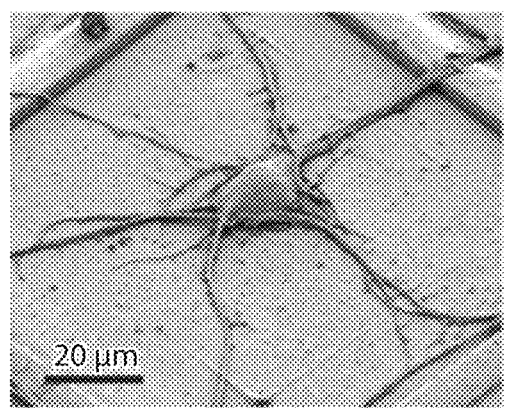

The CMOS-nanowire electrode array chip were then packaged to form a microfluidic well for cell culture (FIG. 15E and FIG. 15F). Live assay fluorescent imaging (FIG. 15E and FIG. 15F) and electrophysiology experiments showed that the device was capable of repeated operation and extended culture times of up to 14 days. For experimentation, the device was plugged into a custom designed printed circuit board (PCB) that contained auxiliary circuits and interfaced to a computer with custom software. The experimental setup accommodated a patch pipette and fluorescent microscope, whose purpose was to verify the workings of the CMOS-nanowire electrode array in electrophysiology experiments.

Figure 16A:
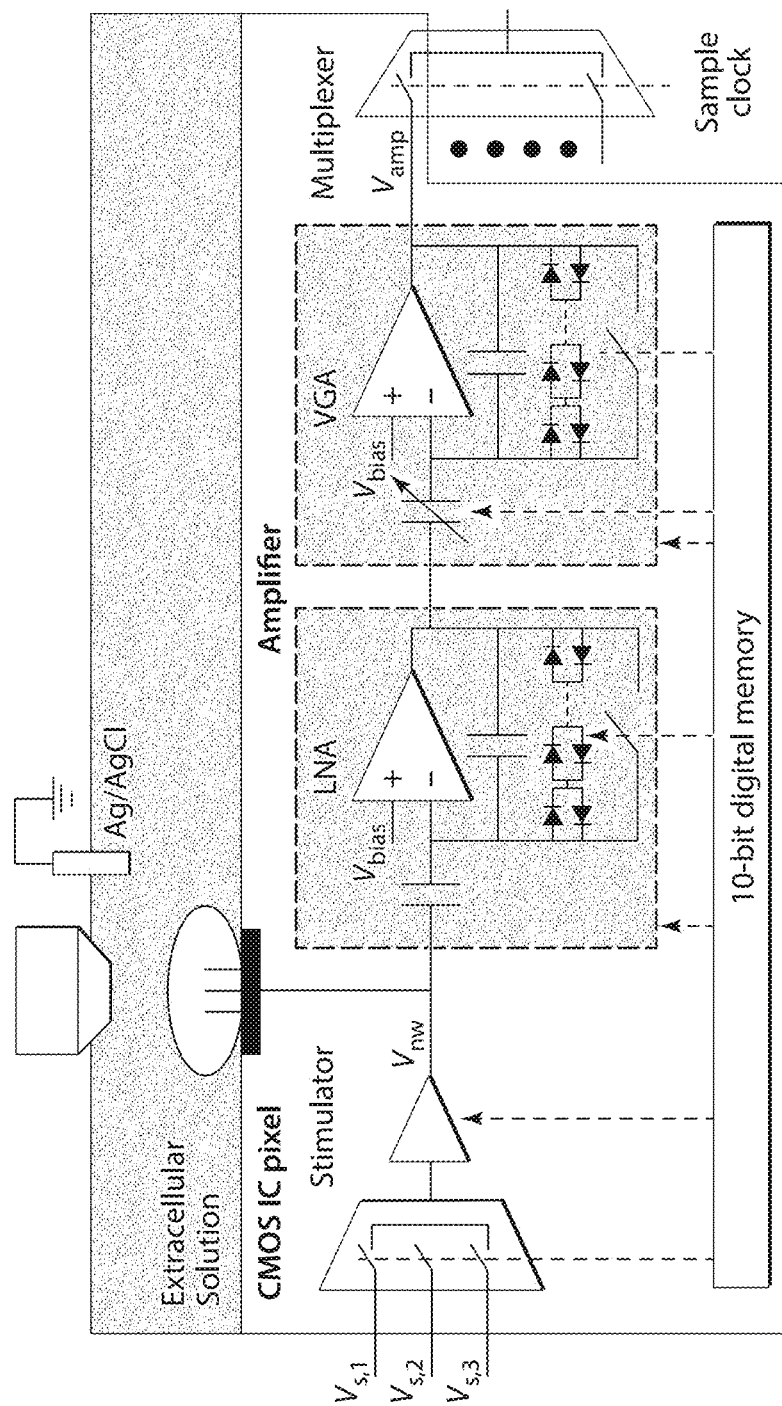
FIGS. 16A-16F illustrate circuitry and nanowires devices, in certain embodiments of the invention.

The design of the CMOS pixel circuitry in the device presented challenges due to the high impedance (~gigaohms) intracellular nanoelectrodes to which it had to interface (FIG. 16A). The impedance of the CMOS pixel amplifier was maximized to minimize signal attenuation, while DC current drawn through the nanoelectrodes was minimized to prevent or reduce adverse effects on cell viability. This was compounded by the general challenge of electrophysiology, for example, the low spectral contents of the electrophysiological signal (1 Hz~5 kHz) where the 1/f noise of electronics is appreciable. These corresponded to design tradeoffs between sensitivity, linearity, and spatial resolution (transistor sizing).

Figure 16B:
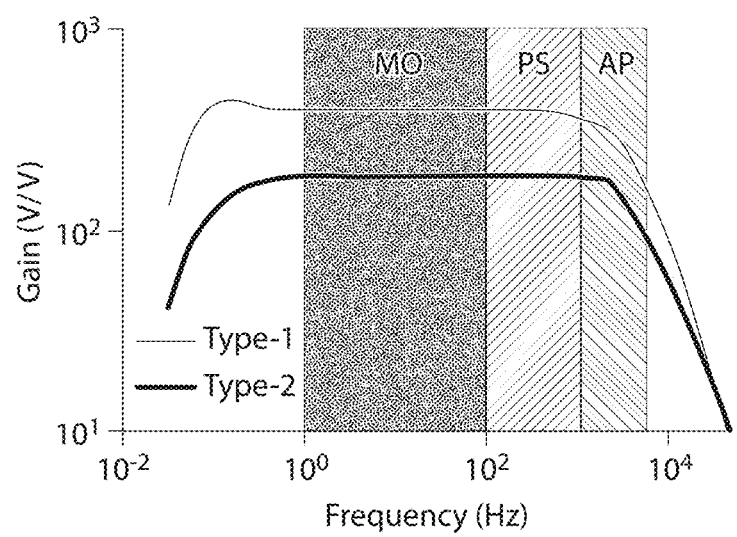
Figure 16C:
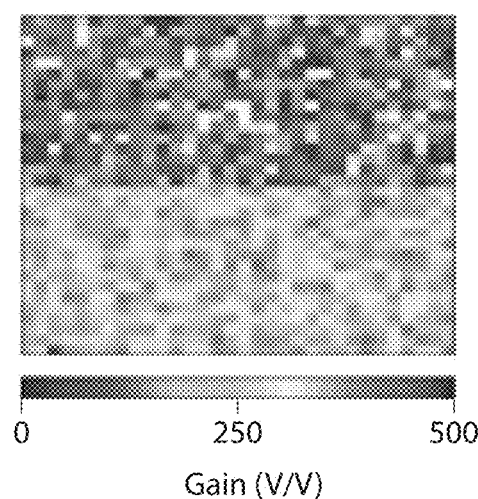
Figure 16D:
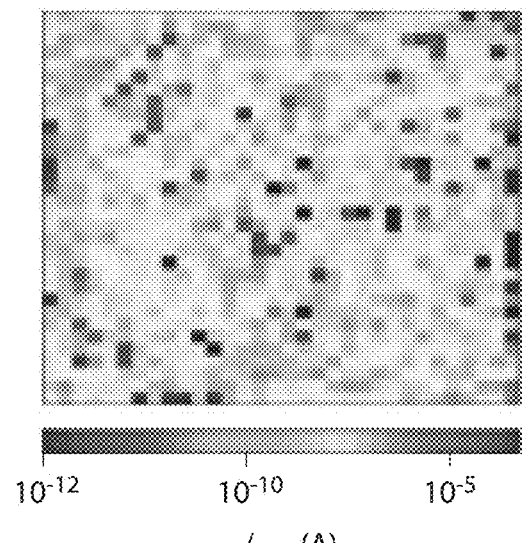

The pixel circuit of FIG. 16A includes a pixel amplifier within a 126 micron×126 micron pixel, with a bandpass filter configuration (FIG. 16A): the low frequency (~0.1 Hz) and high frequency (~5 kHz) poles filtered out much of the 1/f noise and prevented DC current flow while the passband gain, set by the feedback to input capacitor ratio, allowed linear gain through the nanoelectrodes' double layer capacitance. Measurements of the pixel amplifier showed uniform gain across the target frequency range and across the 32×32 array (FIGS. 16B and 16C) where the input referred noise was on the order of ~250 $uV_{rms}$. Aside from the amplifier, each pixel contained a buffer for cell stimulation, a memory for pixel configuration, and an output analog multiplexer to sample the array of pixels simultaneously at 9.75 kHz. Typically, more than 90% of the pixels were available for electrophysiological experiments using these devices, determined by each pixel's electrical characteristics such as passband gain (FIG. 16C) and nanowire electrode conductance (FIG. 16D).

Figure 16E:
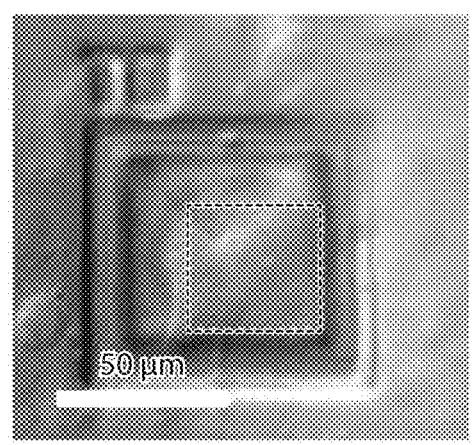
Figure 16F:
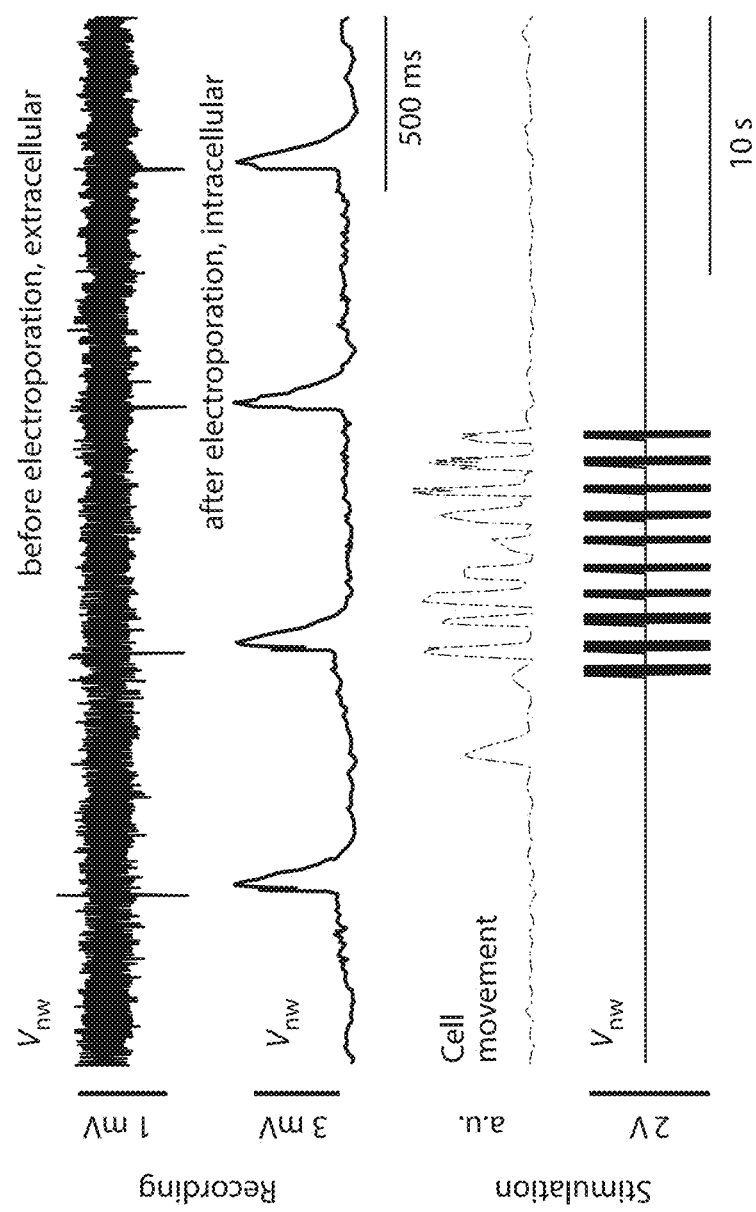

To verify the pixel circuit's functions and the NWE's intracellular capability, experiments were performed using single isolated NRVMs (FIG. 16E). With a beating NRVM on top of a pixel's nanowires, the pixel amplifier readily measured extracellular action potential spikes (FIG. 16E, top right). The amplitude of these extracellular signals was in the range of 250 uV to 1.5 mV, higher than typical planar extracellular electrodes and most likely enhanced by an increased seal resistance due to the NWE's vertical geometry. To gain intracellular access (FIG. 16E, middle right), an electroporation signal (3 trains of 5×1.2 V biphasic pulses at 20 Hz) was applied using the pixel stimulator to permeabilize the membrane allowing for intracellular measurement with signal amplitudes ranging from less than 1 mV to 25 mV. Spontaneous penetration without electroporation was rare but was observed at 1 least once. The measured intracellular shape resembled those of other reported NRVM action potential waveforms; similar recording waveforms were obtained after the addition of a mechanical decoupler, 3 uM blebbistatin, to eliminate mechanical artifacts with patch clamp measurements using HEK293 in vitro cultures validating our linear intracellular transfer function. In addition to recording, the pixel could also excite the NRVMs to fire action potentials by applying voltage pulses using the stimulator after intracellular access has been gained. As an intracellular prosthetic demonstration, the beating frequency of an isolated NRVM was increased from ~1/20 Hz to 1 Hz by applying a biphasic voltage pulse sequence every 1 s with concurrent mechanical movements being observed (FIG. 16E, bottom right).

Figure 17A:
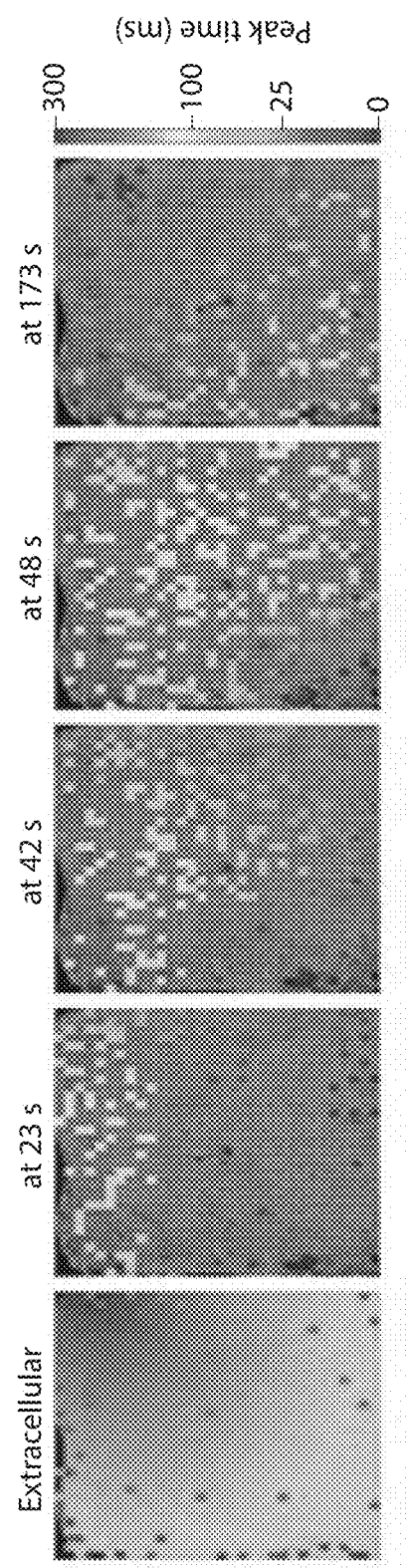
FIGS. 17A-17E illustrate the investigation of tissue cultures, using certain embodiments of the invention.
Figure 17B:
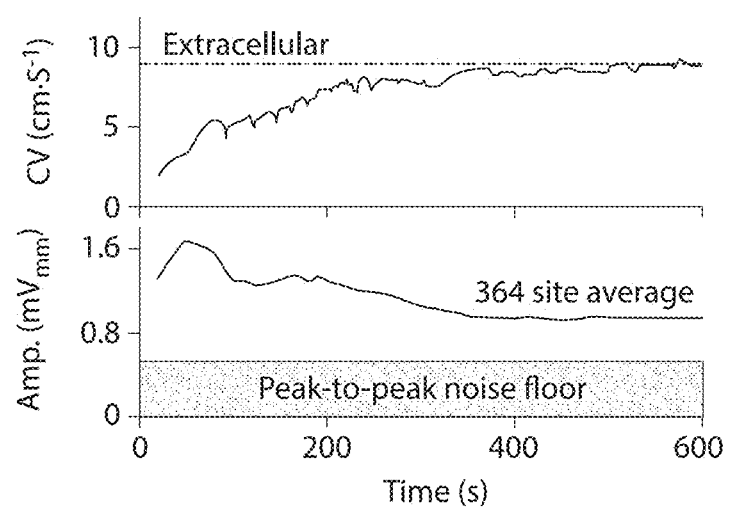
Figure 17C:
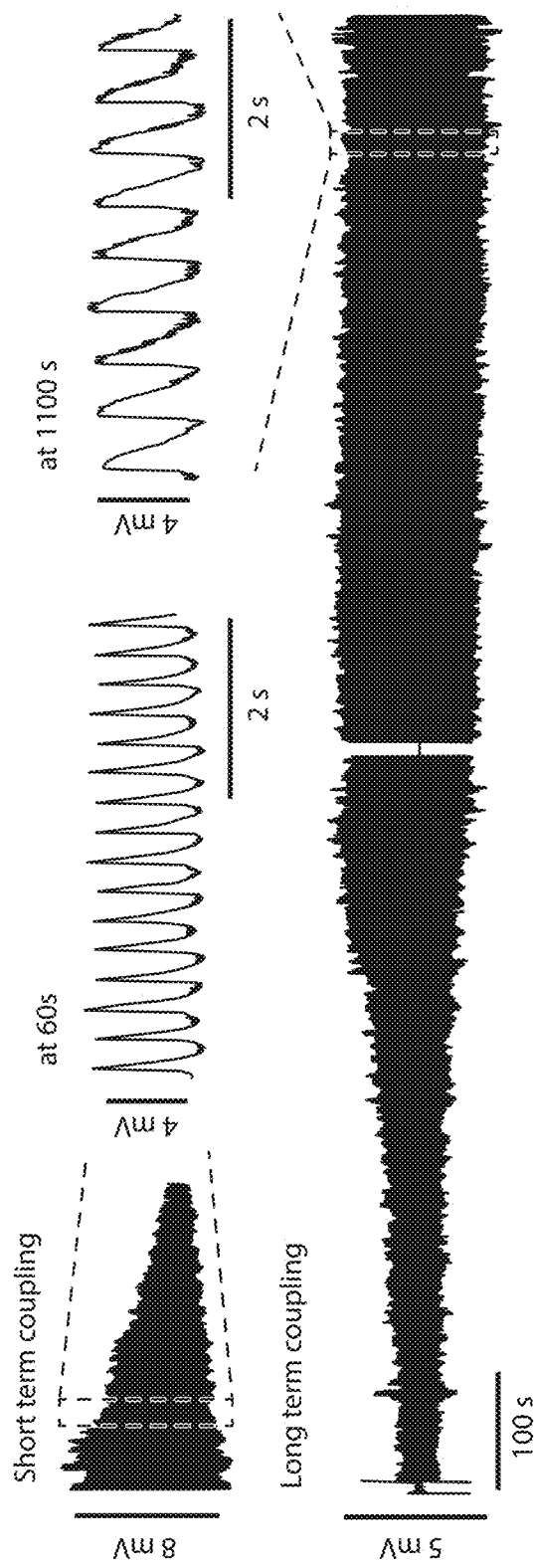
Figure 17D:
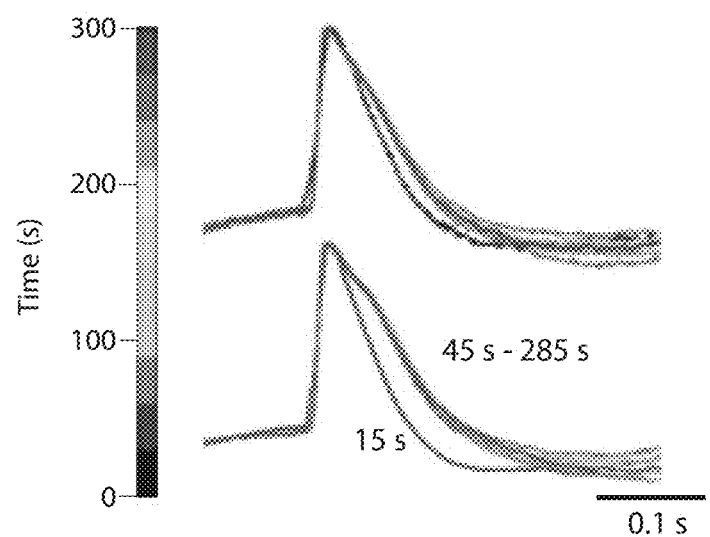
Figure 17E:
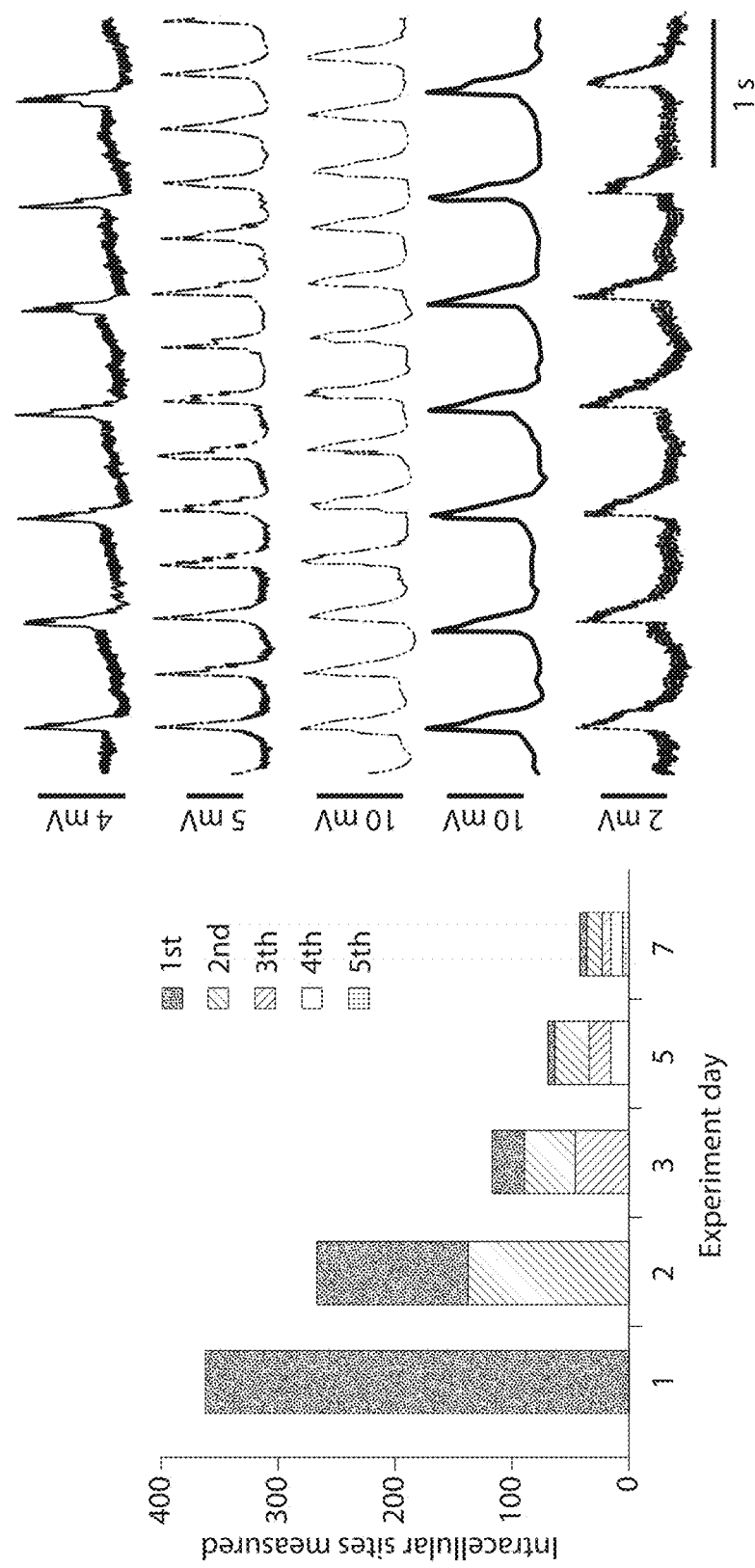

After single-pixel verification, network level recording was performed on beating monolayer-dominated in vitro NRVM tissue cultures to investigate the device's capability for parallel electrophysiology. Extracellular recordings from 968 pixels were first performed where the tissue showed a spatially homogenous propagation across the tissue (FIG. 17A, left) at a conduction velocity (CV) of 9 cm/s (FIG. 17B). Electroporation was then simultaneously performed across all pixels to gain intracellular access. Measurements from 364 cells in total (35% coupling efficiency) were used to map the intracellular network dynamics of the tissue (FIG. 17A) and calculate CV (FIG. 17B). Initially, a spiral pattern around the peripheral and a reduction of CV to 2 cm/s were observed. The culture then recovered back to its original homogeneous propagation and CV in ~3 min. This resultant pattern was attributed to leakage currents caused by electroporation slowing, or halting, wave propagation in the central tissue with eventual recovery due to the resealing of the membrane. The coupling amplitude of the intracellular signal further corroborated this as it initially decayed over time (FIG. 17B, bottom and FIG. 17C, top), presumably due to the cell membrane resealing over the top of the NWE preventing further intracellular measurement. Other pixels, however, exhibited coupling for more than 20 min (FIG. 17C, bottom), resulting in the plateau of the coupling amplitude in FIG. 17B. In this case, the cell membrane likely resealed around the base of the NWE keeping the tip exposed to the intracellular solution for long term, stable recordings. Regardless of short term or long term coupling, throughout the resealing process, the action potential waveform shape remained relatively stable with action potentials after 45 s remaining constant (FIG. 17D). Further chronic studies showed that the intracellular access could be regained on subsequent days; 5 total experiments were performed on the same culture over the course of 7 days (FIG. 17E). Using the network level extracellular and intracellular capabilities of the device, the effects of various drugs on NRVM tissue were then characterized using these devices (FIG. 18). Extracellular access can be used for network level analysis during drug applications, such as determination of oscillation frequency and CV, with minimal invasiveness. Action potential waveform shape can too be investigated using extracellular data, as the repolarization slope can cause a smaller yet measurable extracellular signal. Due to variations in seal resistance and electrode to electrode variations, however, the degree and amount of extracellular signal distortion could vary. Intracellular measurements, however, allow for accurate measurement of waveform shape and characteristics such as action potential duration (APD). The capability of the device to perform either extracellular or intracellular interrogation, or both, with minimal experimentation effort realized through CMOS electronics and automated recording software, offers promise for high throughput, whole tissue pharmaceutical drug screening.

Figure 18A:
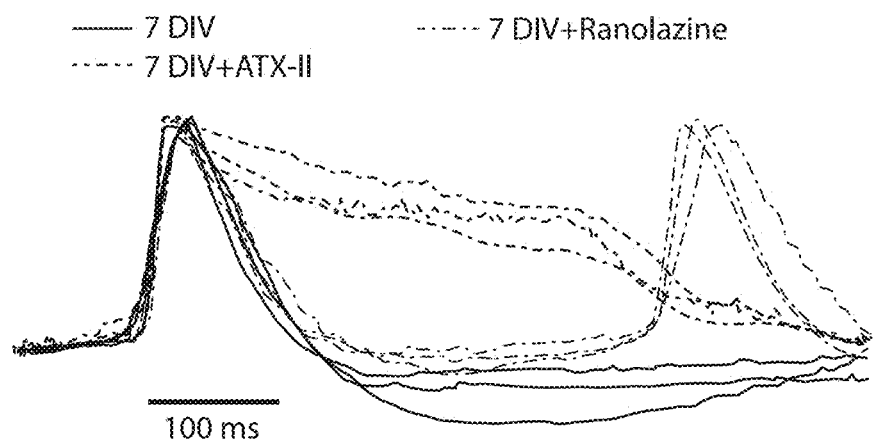
FIGS. 18A-18E illustrate various action potentials determined in various embodiments of the invention.
Figure 18B:
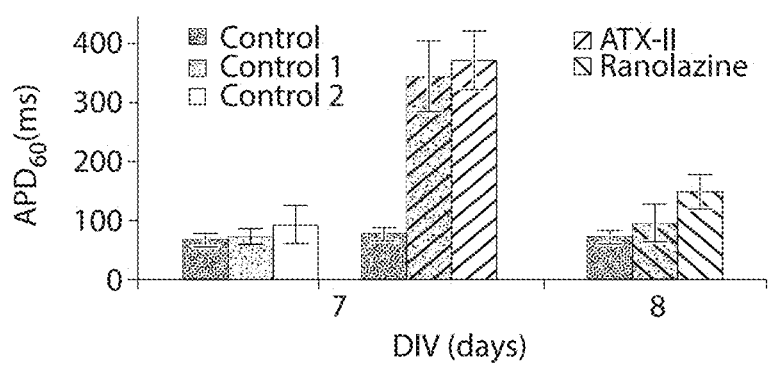
Figure 18C:
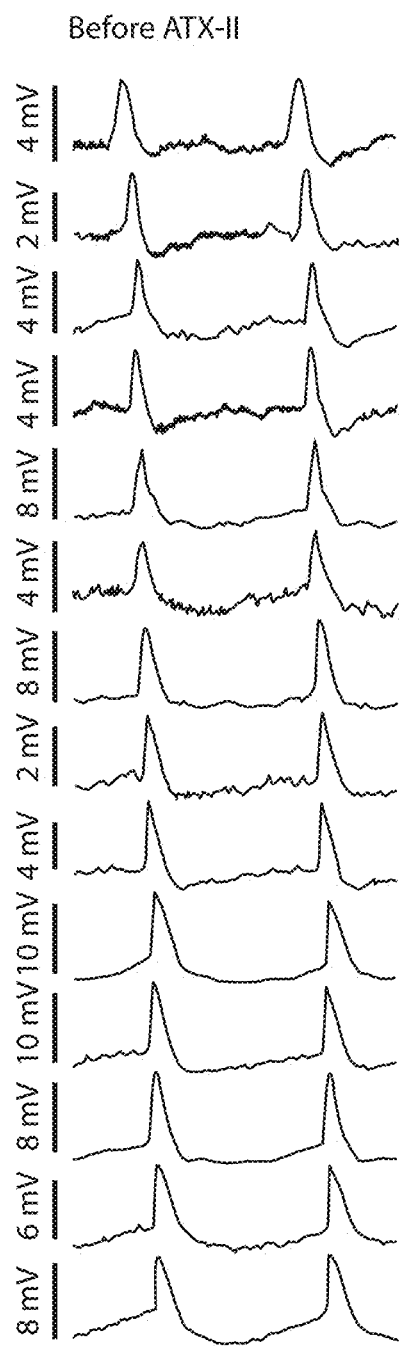
Figure 18D:
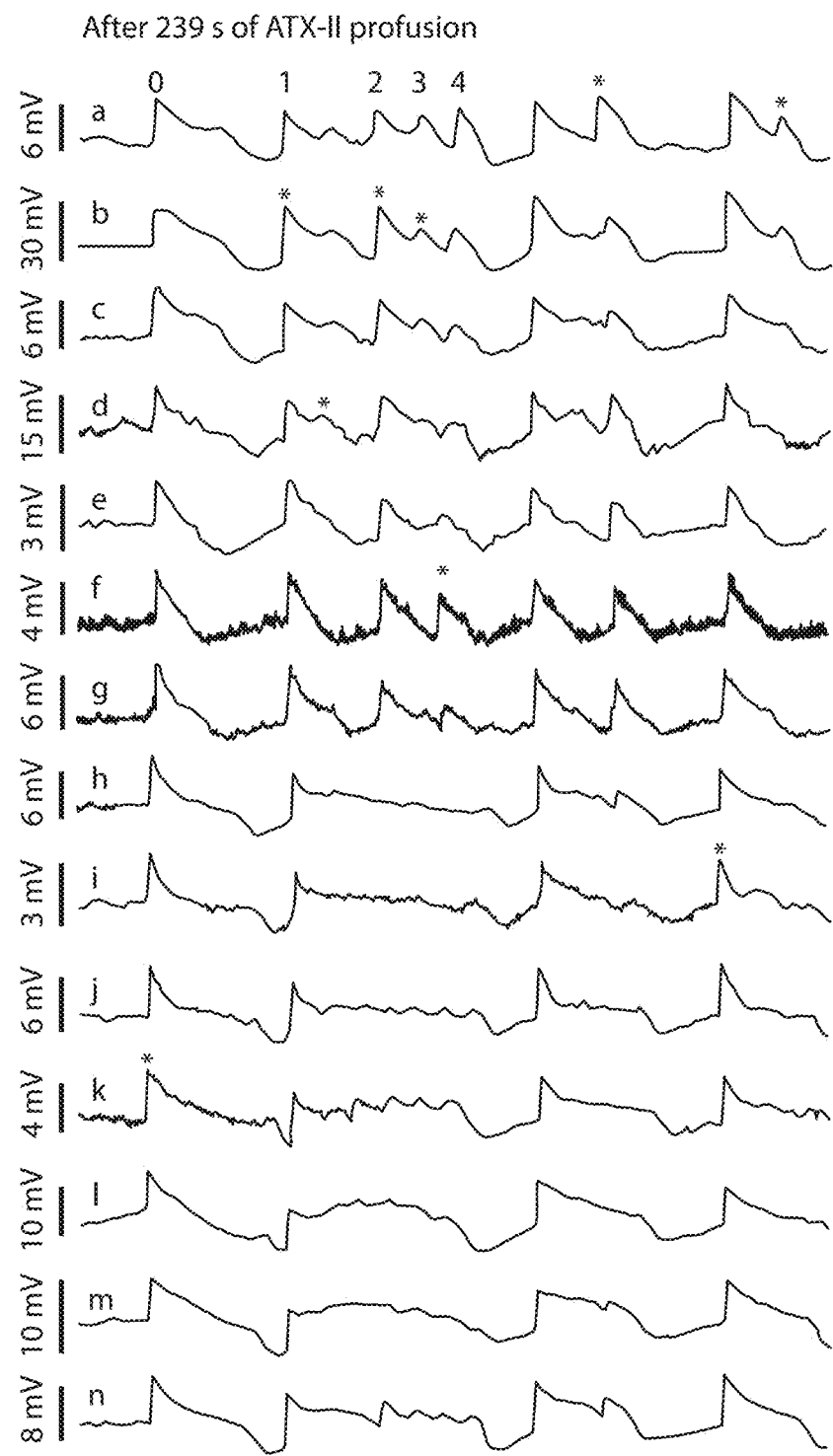
Figure 18E:
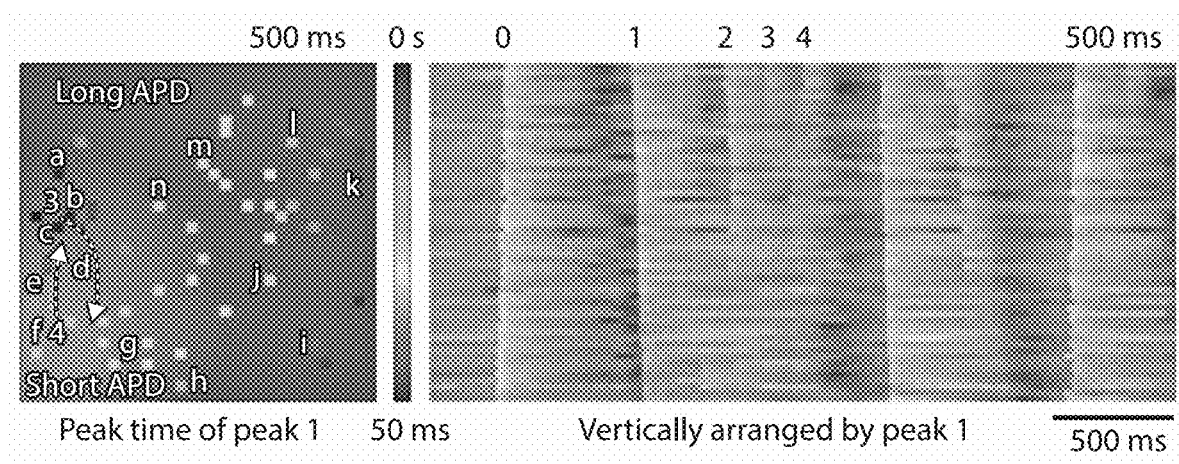

With the intracellular network-level recording capability, it was also possible to monitor the development of drug induced arrhythmias, triggered activity (TA), and propagation of early after depolarizations (EADs) within NRVM tissue (FIG. 18D and FIG. 18E). A Na ion channel toxin, ATX-II, which causes a delayed inactivation of the fast Nav1.5 channel was used, mimicking the effects of genetic mutations to the gene SCNSA which codes the Nav1.5 protein and results in congenital long-QT syndrome type 3. Being able to investigate this type of drug effect is paramount during preclinical development as drug-induced long-QT syndrome and arrhythmias are the most common cause of withdrawal or restriction of marketed drugs. During the experiment, a constant increase in APD was observed with the emergence of TA and EADs after 239 s of drug profusion. The origin of these EADs and TA had spatial correlation; the right half of the tissue experienced propagating phase 2 EADs (pixels j-m) after peak 1 resulting in distinct regions of long (pixels h-n) and short (pixels e-g) APD in the tissue, with a transitional region in between (pixels a-d). As the short APD region repolarized after peak 1, however, a second action potential (peak 2) fired but was unable to propagate through the whole tissue due to the still depolarized long APD region, marking the onset of an arrhythmia within the tissue. An EAD in the transition region then propagates causing TA in the short APD region (pixel f), with back propagation in the transitional region as an EAD (peak 4). The origin of the EAD in the transition zone complied and supported the mechanism of an extrinsic EAD caused by a repolarization gradient between regions with short and long APD. Furthermore, the reduced velocity of this back-propagation (1.8 cm/s compared to 6.7 cm/s for forward-propagating peak 1) indicated a transition of $I_{Na}$-mediated propagation to $I_{Ca,L}$-mediated propagation, supporting the ability of bi-stable wave propagation in cardiac tissue. These latter findings accentuate the ability of the device to both analyze sub-threshold events in individual cells and track network dynamics across a large number of cells.

This example shows parallel intracellular interrogation, combining the intracellular capability of NWEs with the scalability of CMOS IC technology. Harnessing advances in CMOS fabrication techniques, it is possible to implement a larger number of pixels and smaller pitch size for higher spatial resolution.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus for electrically communicating with a cell, comprising:
   a silicon substrate having a top surface configured to face the cell;
   a plurality of connection sites disposed on the top surface and configured to be in electrical communication with the cell via a plurality of conductive surfaces of the plurality of connection sites; and
   an integrated circuit disposed in the silicon substrate underneath the top surface and in electrical contact with the plurality of the connection sites, the integrated circuit comprising at least one amplifier unit and at least one stimulator unit.

2. The apparatus of claim 1, wherein the integrated circuit comprises at least about 1,000 connection sites.

3. The apparatus of claim 1, wherein a first connection site of the plurality of connection sites is connected to the at least one amplifier unit and the at least one stimulator unit.

4. The apparatus of claim 3, wherein the at least one amplifier unit comprises a first amplifier unit and a second amplifier unit, the at least one stimulator unit comprises a first stimulator unit and a second stimulator unit, and wherein
   the first connection site of the plurality of connection sites is connected to the first amplifier unit and the first stimulator unit, and
   a second connection site of the plurality of connection sites is connected to the second amplifier unit and the second stimulator unit.

5. The apparatus of claim 1, wherein the integrated circuit comprises an array of at least about 25 amplifier units, at least about 25 stimulator units, or at least about 25 amplifier units and at least about 25 stimulator units.

6. The apparatus of claim 1, wherein the at least one stimulator unit comprises a plurality of voltage stimulus sources.

7. The apparatus of claim 6, wherein the at least one stimulator unit comprises at least one multiplexer configured to selectively connect one or more voltage stimulus sources of the plurality of voltage stimulus sources to a connection site of the plurality of connection sites.

8. The apparatus of claim 7, wherein the integrated circuit further comprises a digital memory in electrical communication with the at least one stimulator unit and the at least one amplifier unit.

9. The apparatus of claim 8, wherein the digital memory is configured to send one or more signals to enable the at least one multiplexer and one or more voltage stimulus sources of the at least one stimulator unit, and to disable one or more amplifiers in the at least one amplifier unit.

10. The apparatus of claim 8, wherein the digital memory is configured to send one or more signals to disable the at least one multiplexer and one or more voltage stimulus sources of the at least one stimulator unit, and to enable one or more amplifiers in the at least one amplifier unit.

11. The apparatus of claim 1, wherein the integrated circuit further comprises an output multiplexer coupled to the at least one amplifier unit, the output multiplexer configured to receive a plurality of recording signals representative of an electrical characteristic at some or all of the plurality of connection sites and to generate an output signal based on the plurality of recording signals.

12. The apparatus of claim 8, wherein the at least one stimulator unit is disposed side by side in the silicon substrate with the at least one amplifier unit.

13. The apparatus of claim 1, wherein the amplifier unit comprises a variable gain amplifier (VGA).

14. The apparatus of claim 1, wherein the plurality of connection sites comprise an array of metal pads disposed on the top surface, and the integrated circuit comprises an array of pixel circuits, each pixel circuit comprises at least one amplifier unit and at least one stimulator unit, and wherein each metal pad is connected to a corresponding pixel circuit.

15. The apparatus of claim 14, wherein for each pixel circuit of the array of pixel circuits:
the at least one amplifier unit comprises a pixel amplifier having an area of no more than 500 μm by 500 μm.

16. The apparatus of claim 1, wherein the integrated circuit comprises CMOS transistors having a characteristic dimension of 0.35 μm or less.

17. The apparatus of claim 1, wherein each of the plurality of conductive surfaces of the plurality of connection sites comprises a metal pad.

18. The apparatus of claim 1, further comprising a plurality of upstanding nanowires in contact with the plurality of conductive surfaces of the plurality of connection sites, the plurality of upstanding nanowires configured to be in electrical communication with the cell.

19. The apparatus of claim 18, wherein the plurality of connection sites are configured to be in electrical communication with the cell via the plurality of upstanding nanowires.

\* \* \* \* \*

UNITED STATES PATENT AND TRADEMARK OFFICE
CERTIFICATE OF CORRECTION

| | |
|---|---|
| PATENT NO. | : 11,833,346 B2 |
| APPLICATION NO. | : 17/144387 |
| DATED | : December 5, 2023 |
| INVENTOR(S) | : Hongkun Park et al. |

It is certified that error appears in the above-identified patent and that said Letters Patent is hereby corrected as shown below:

In the Specification

At Column 1, Lines 24-28, please change the paragraph:
"This invention was made with government support under Grant No. 8DP1DA035083-05 awarded by the National Institutes of Health and under Grant No. W911NF-15-1-0565 awarded by the U.S. Army Research Office. The government has certain rights in the invention."

To:
-- This invention was made with government support under DA035083 awarded by the National Institutes of Health, and W911NF-15-1-0565 awarded by the Army Research Laboratory - Army Research Office. The government has certain rights in the invention. --

Signed and Sealed this
Thirteenth Day of August, 2024

Katherine Kelly Vidal
*Director of the United States Patent and Trademark Office*